US012605518B2

(12) United States Patent (10) Patent No.: US 12,605,518 B2
Luo (45) Date of Patent: Apr. 21, 2026

(54) GAS PASSAGE FOR USE IN A PAP DEVICE

(71) Applicant: WALLENBERG UNION LLC, Newark, DE (US)

(72) Inventor: David Luo, Newark, DE (US)

(73) Assignee: WALLENBERG UNION LLC, Newark, DE (US)

( * ) Notice: Subject to any disclaimer, the term of this patent is extended or adjusted under 35 U.S.C. 154(b) by 0 days.

(21) Appl. No.: 18/778,376

(22) Filed: Jul. 19, 2024

(65) Prior Publication Data

US 2026/0021262 A1     Jan. 22, 2026

(51) Int. Cl.
*A61M 16/00* (2006.01)
*F04D 29/66* (2006.01)

(52) U.S. Cl.
CPC ....... *A61M 16/0066* (2013.01); *F04D 29/667* (2013.01); *A61M 2205/42* (2013.01); *A61M 2206/14* (2013.01); *F04D 29/663* (2013.01)

(58) Field of Classification Search
CPC .......... A61M 16/0066; A61M 2205/42; A61M 2206/14; F04D 29/663; F04D 29/665; F04D 29/667; A62B 18/006; A62B 18/045
See application file for complete search history.

(56) References Cited

U.S. PATENT DOCUMENTS

| | | | | |
|---|---|---|---|---|
| 12,322,364 B1* | 6/2025 | Ke | ...................... | G10K 11/172 |
| 2009/0007912 A1* | 1/2009 | Lindell | ................. | A61M 16/10 |
| | | | | 128/204.18 |
| 2013/0263854 A1* | 10/2013 | Taylor | ............... | A61M 16/0066 |
| | | | | 128/204.23 |
| 2015/0023782 A1* | 1/2015 | Velzy | ................... | F04D 29/701 |
| | | | | 415/119 |

(Continued)

FOREIGN PATENT DOCUMENTS

| | | | | | |
|---|---|---|---|---|---|
| CN | 117350099 A | * | 1/2024 | .......... | F04D 29/663 |
| CN | 117942468 A | * | 4/2024 | ........ | A61M 16/0057 |
| EP | 0872643 A2 | * | 10/1998 | ......... | F04D 29/4213 |

OTHER PUBLICATIONS

Machine translation of CN-117350099-A (Year: 2024).*

(Continued)

*Primary Examiner* — Joseph D. Boecker
(74) *Attorney, Agent, or Firm* — Birch, Stewart, Kolasch & Birch, LLP

(57)     ABSTRACT

A gas passage for use in a PAP device configured to provide pressurized gas to a patient, including a passage casing with an air intake and an air outlet. The casing is configured to encompass and accommodate internal components and forms a chamber inside, where the chamber is configured to facilitate the flow and accumulation of gas. A blower is provided within the chamber to pressurize and output the gas. The internal components of the noise-reducing gas (Continued)

passage include noise reduction components configured to attenuate the noise of the gas entering the noise-reducing gas passage. These noise reduction components include a ventilation component, an intake pipe, and a flexible component at the air intake. Additionally, this disclosure specifies scientific and precise data requirements for the internal structure and positioning of the blower and noise-reducing components within the noise-reducing gas passage to achieve effective and excellent noise reduction.

25 Claims, 27 Drawing Sheets

(56)                     References Cited

U.S. PATENT DOCUMENTS

| 2015/0320954 | A1* | 11/2015 | Suzuki | F04D 25/062 |
| | | | | 128/205.25 |
| 2018/0193577 | A1* | 7/2018 | Cariola | A61M 16/161 |
| 2020/0188616 | A1* | 6/2020 | Kenyon | A61M 16/0066 |
| 2023/0233780 | A1* | 7/2023 | Zhi | A61M 16/0066 |
| 2023/0398318 | A1* | 12/2023 | Mazzone | A61M 16/0066 |
| 2024/0358942 | A1* | 10/2024 | Poirot | A61M 16/0063 |
| 2025/0041547 | A1* | 2/2025 | Zhi | A61M 16/0066 |

OTHER PUBLICATIONS

Machine translation of EP-0872643-A2 (Year: 1998).*
Co-pending U.S. Appl. No. 18/783,681.*
Co-pending U.S. Appl. No. 18/784,481.*
Machine translation of CN-117942468-A.*

* cited by examiner

6

6

PAP Device

GAS PASSAGE FOR USE IN A PAP DEVICE

TECHNICAL FIELD

This disclosure pertains to a gas passage within a Positive Airway Pressure (PAP) device configured to improve respiratory system-related disorders, such as sleep apnea.

BACKGROUND

Snoring is a common sleep phenomenon, specifically characterized by the sharp, piercing noise produced by the vibration of soft tissues in the throat. As people age, this problem becomes increasingly prevalent and pronounced. Research indicates that habitual snoring affects 15.6% to 19% of the European population, with occasional snorers making up 26% to 30%. These figures reflect the widespread and common nature of this phenomenon. Causes of snoring include respiratory diseases, ear, nose, and throat illnesses, oral diseases, and endocrine disorders, among which obstructive sleep apnea hypopnea syndrome is included. In addition to snoring, obstructive sleep apnea hypopnea syndrome increases the risk of cardiovascular diseases, hypertension, heart disease, and stroke. Moreover, sleep apnea is not merely a noise-making issue; it can lead to a range of social and health problems. Sufferers may often feel tired and even experience headaches or a sensation of choking upon waking in the morning. Sleep apnea can lead to insufficient oxygen supply; during apnea episodes, the oxygen level in the patient's body drops, triggering a stress response to maintain organ vitality. This response can lead to increased breathing difficulty, accelerated heart rate, increased cardiac output, dizziness, and headaches by boosting oxygen intake to raise blood oxygen levels. Over time, sleep apnea significantly affects sleep quality and continuous stress responses can put excessive pressure on the heart and blood vessels. Patients might be frequently disturbed by sleep apnea, noise, and irregular breathing during sleep. Frequent apneas can wake the patient from deep sleep stages multiple times, disrupting the normal sleep cycle, affecting sleep continuity and depth, and consequently impacting daytime attention, concentration, and work efficiency. Reduced sleep quality can impair emotional regulation in the brain, increasing the risk of anxiety, depression, and other mental health issues. Additionally, the noise from snoring due to apnea can disturb a partner's sleep, preventing them from getting adequate rest. In the long run, this can lead to emotional fluctuations, fatigue, and mental stress in the partner, thereby affecting the quality of the relationship. Moreover, the individual may also experience emotional fluctuations, anxiety, depression, and decreased self-esteem, all attributable to sleep apnea.

One fundamental cause of sleep apnea is the relaxation of the soft tissues in the throat, particularly in the soft palate area at the back of the mouth. While awake, a patient's muscles are typically tense, keeping the airway open and clear. However, as the patient enters deep sleep, the muscles begin to relax, especially the soft tissues in the throat, leading to partial airway blockage and vibrations that produce the sound of snoring. Additionally, the relaxed muscles can narrow the upper airway, further increasing the frequency of vibrations and the severity of snoring.

Overall, although snoring is a common issue, it can have negative impacts on the individual and their environment, including health problems, social distress, and a decline in sleep quality. Most importantly, snoring is likely to lead to conditions such as sleep apnea. Therefore, enhancing awareness and understanding of snoring and sleep apnea symptoms, as well as implementing effective treatments or preventive measures, is crucial for improving sleep quality and overall life quality. Through scientific and comprehensive methods and strategies, it is possible to effectively manage and alleviate issues related to snoring and sleep apnea, improving patients' quality of life and health.

SUMMARY

The objective of this disclosure is to provide a novel gas passage for use in PAP devices, utilizing optimizations in its structure and the interaction of its components to achieve superior operational effects on an existing basis, and to facilitate the manufacturing of the gas passage and its rapid adaptation to the market. This disclosure describes an effective structure that reduces noise within the smallest possible volume of the gas passage and overcomes the limitations present in existing similar products. Thus, it offers a more effective solution with broader application scenarios and space, providing a safer method of delivering positive pressure airflow to the patient's respiratory system for the treatment of sleep breathing disorders.

This disclosure provides a gas passage for use within a PAP device, and the gas passage includes: a passage casing having at least one air intake and at least one air outlet, configured to encompass and accommodate internal components; at least two chambers configured to provide spaces for gas flow and accumulation; a blower provided within one of the at least two chambers, having an inlet to receive gas and an outlet to allow the gas to flow out; and at least one ventilation component configured to communicate with the at least two chambers to allow gas to flow through the at least one ventilation component within the at least two chambers. In addition, the gas forms a primary flow path from the at least one air intake of the passage casing to the at least one air outlet, the path having at least three height differences.

In an embodiment, the at least one ventilation component within the noise-reducing gas passage takes the form of several ventilation components combined together.

In an embodiment, the at least one ventilation component includes at least one baffle, and the at least one baffle of the ventilation component is configured to have inclined surfaces.

In an embodiment, the passage casing includes an inner wall, and the blower is provided at least 4 mm away from the inner wall of the passage casing.

In an embodiment, a direction of the gas passing through the at least one ventilation component is parallel or perpendicular to a direction of the gas entering the blower.

In an embodiment, a length of the primary flow path is at least 160 mm.

This disclosure provides another gas passage for use within a PAP device, and the gas passage includes: a passage casing having at least one air intake and at least one air outlet, configured to encompass and accommodate internal components; at least two chambers configured to provide spaces for gas flow and accumulation; a blower provided within the one of the at least two chambers, having an inlet to receive gas and an outlet to allow the gas to flow out; and at least one ventilation component, configured to communicate with the at least two chambers to allow gas to flow through the at least one ventilation component within the at least two chambers, wherein the length-to-width ratio of the at least one ventilation component is between 0.1 to 1. Gas flows from the at least one air intake of the passage casing to the at least one air outlet to form a primary flow path with a height difference.

In an embodiment, the passage casing has an inner wall, the at least one ventilation component is provided only within at least one of the two chambers, and the at least one ventilation component includes a first end to allow gas entry and a second end to allow gas exit, both ends having a distance of at least 5 mm from the inner wall of the passage casing.

In an embodiment, the at least one ventilation component includes baffles, and a spacing between each of the baffles is between 0.8 mm to 2.2 mm.

In an embodiment, a height of the at least one ventilation component is at least 10 mm.

In an embodiment, gas enters the inlet of the blower either in a straight manner or in a rotation direction of the blower.

In an embodiment, the at least one ventilation component is configured to be integrally formed with the passage casing.

This disclosure provides yet another gas passage for use within a PAP device, and the gas passage includes: a passage casing having at least one air intake and at least one air outlet, configured to encompass and accommodate internal components; at least two chambers configured to provide spaces for gas flow and accumulation; a blower provided within one of the at least two chambers, having an inlet to receive gas and an outlet to allow the gas to flow out; and at least one ventilation component, configured to communicate with the at least two chambers to allow gas to flow through the at least one ventilation component within the at least two chambers. An axial line of the at least one air intake of the passage casing is not parallel to an axial line of the inlet of the blower; and gas flows from the at least one air intake of the passage casing to the at least one air outlet to form a primary flow path with a height difference.

In an embodiment, the at least one air intake is configured to have a flexible component including flexible material.

In an embodiment, an intake pipe connectable to the at least one air intake is provided at the at least one air intake, and a length of the intake pipe is between 25 mm to 80 mm.

In an embodiment, the intake pipe is provided at an edge part of the gas passage.

In an embodiment, a volume of one of the at least two chambers that house the blower is at least three times a volume of the blower.

In an embodiment, the passage casing includes one of the following materials: polypropylene (PP), polycarbonate (PC), polyethylene terephthalate glycol-modified-1,4-cyclo-hexanedimethanol ester (PCTG), polyamide (PA), or polyetheretherketone (PEEK).

This disclosure also provides another gas passage for use within a PAP device, and the gas passage includes: a passage casing having at least one air intake and at least one air outlet, configured to encompass and accommodate internal components; at least two chambers configured to provide spaces for gas flow and accumulation; a blower provided within one of the at least two chambers, having an inlet to receive gas and an outlet to allow the gas to flow out, wherein the inlet is configured to communicate with one of the at least two chambers that does not house the blower; and at least one ventilation component, configured to communicate with the at least two chambers, having an inlet end for gas entry and an outlet end for gas exit, wherein both ends are at a distance greater than or equal to 3.45 mm from an inner wall of the passage casing. Gas flows from the at least one air intake of the passage casing to the at least one air outlet to form a primary flow path with at least one height difference. Moreover, an intake pipe connectable to the at least one air intake is provided at the at least one air intake, configured to communicate an external environment with an interior of the passage casing, and the at least one air outlet is configured to be connectable to an outlet pipe provided at the at least one air outlet and configured to receive pressurized airflow from the outlet of the blower, the intake pipe having at least one of the following characteristics:

a. the intake pipe having a draft angle, and the angle is greater than or equal to 0.1°;

b. a length of the intake pipe being between 25 mm to 80 mm.

In an embodiment, a distance between the blower and the inner wall of the passage casing is at least 4 mm.

In an embodiment, a volume of one of the at least two chambers that house the blower is at least three times a volume of the blower.

In an embodiment, an axial line of the intake pipe is perpendicular to an axial line of the inlet of the blower.

In an embodiment, a ratio of an opening area of the outlet pipe to an area of the outlet of the blower is between 85% to 110%.

In an embodiment, the axial lines of the intake pipe and the outlet pipe have different orientations.

In an embodiment, the outlet pipe is provided with a sealing component connectable to the outlet pipe, and the sealing component is configured to connect the at least one air outlet to the outlet of the blower.

Implementing this disclosure's gas passage offers several beneficial effects:

1. Designing and optimizing multiple structures within the gas passage allows it to achieve superior noise reduction solely through internal structural enhancements. Specifically: (1) Simple and efficient new structures such as ventilation components, intake pipes and flexible components are configured to effectively reduce the noise in each part of the gas passage, respectively, thus achieving better noise reduction in the gas passage. a. The specific structure of the ventilation component in this disclosure includes orderly arranged baffles inside and a peripheral wall that shapes its exterior. Compared to existing noise-reducing structure components in gas passages on the market, the ventilation component of this disclosure is simpler, yet its noise reduction effectiveness is not inferior to existing market components. This design not only helps reduce the propagation of noise in the gas passage but also minimizes cross-interference and turbulence of airflow, facilitating a smoother flow of air through the gas passage and reducing energy loss. b. Additionally, this disclosure has been experimentally proven that a conical gas passage has a certain degree of noise reduction effect. Therefore, an intake pipe is installed at the gas passage's air intake and configured as a conical gas passage to achieve better noise reduction. c. Similarly, a flexible component is configured in the same form as the intake pipe and placed at the air intake where the gas supply enters. Since the flexible component is a separate, single structure, it is made of an elastomeric material to further reduce noise. The noise reduction structures of the ventilation component, the intake pipe, and the flexible component are positioned at different locations within the chamber of the gas passage, effectively reducing noise uniformly across various parts of the gas passage, and minimizing the overall noise emitted from the airway. (2) Digital optimization of the internal structure of the gas passage and strategic planning of the placement of its internal components are conducted to achieve better noise reduction more scientifically. Specifically, limiting the distance between the blower and the inner wall of the casing helps isolate the blower from the casing of the gas passage, thereby reducing vibrations and noise, and preventing the creation of small gaps that could produce noise as gas passes through. By regulating the length-to-width ratio and internal gaps of the ventilation components, the optimal noise reduction effect is achieved for this structural configuration in conjunction with the gas passage. Requirements are made for the distance between each opening of each chamber that provides gas flow into the internal chambers of the gas passage and the opposing inner walls of the casing to ensure there is ample space for gas accumulation and directional changes without causing disorder and turbulence. The optimized casing of the gas passage enhances operational efficiency while also reducing gas pressure and flow consumption. Additionally, placing the air intake and air outlet on different planes of the casing effectively reduces noise from the air intake and ensures that this noise is kept away from the patient's ear area, significantly enhancing the overall comfort of the device. Beyond the mentioned advantages, further optimization of the gas passage design and flow characteristics can significantly improve the stability of the device. This means that performance fluctuations and uncertainties during start-up, operation, and shutdown phases will be greatly reduced, further enhancing the operational stability and reliability of the device. These comprehensive benefits not only improve the long-term stability and performance of the device but also effectively reduce safety risks and potential failure rates during operation. (3) By redesigning and optimizing the internal structure of the gas passage from both planar and three-dimensional perspectives, the path of airflow within the gas passage has been increased to achieve superior noise reduction. The length of airflow directly affects the noise levels within the chamber; shorter airflow paths tend to result in sudden changes in airflow speed and pressure, which can increase the likelihood of noise generation. Conversely, longer airflows gradually slow down the changes in gas speed and pressure over time, thereby reducing noise production. In the planar effect, this disclosure places the blower at the center of the gas passage, causing the airflow entering the chamber housing the blower to flow around it before flowing into other chambers. This arrangement increases the length of the airflow path within the plane, reducing noise. In the three-dimensional effect, in one instance, the internal chambers of the gas passage are designed as upper and lower chambers, allowing the gas to have a vertical path in addition to the planar path. This configuration transforms the airflow path from planar to three-dimensional, noticeably increasing the airflow path. Furthermore, by positioning the ventilation components within the gas passage so that the airflow direction through the ventilation components is vertical, and since the ventilation components are noise-reducing components with a certain height and not on the same plane as the intake and outlet, the airflow from the intake to the outlet undergoes at least three changes in height, meaning the gas flows vertically at least twice. This increases the vertical path and further lengthens the airflow path, providing patients with a quieter and more comfortable user experience.

2. From the patient's perspective, this disclosure not only offers a variety of options but also minimizes the impact on airflow when employing a foamless gas passage design, which not only extends the life of the device but also enhances safety during use. a. In devices utilizing a foamless design, the internal structure of the gas passage has been optimized to significantly reduce airflow resistance. Firstly, through geometric design and streamlined structures with large rounded corners, the space within the gas passage is maximized, ensuring that airflow can move smoothly without obstruction. Secondly, the smooth surface of the inner walls of the gas passage reduces friction between the airflow and the inner walls. This not only increases the speed of air circulation but also helps reduce energy consumption, thereby enhancing the overall performance and efficiency of the device. b. Furthermore, in terms of safety, foamless design is more beneficial for respiratory safety. According to some cases, such as recall events from a certain brand, foam materials used over a long period may release harmful particles under specific conditions, and might even pose a carcinogenic risk. Additionally, if the device is improperly cleaned or stored for long periods in hot and humid conditions, foam materials may degrade and emit harmful gases. Eliminating foam from the design also effectively reduces potential issues with microbial growth and the accumulation of other contaminants within the device. Such design not only raises the hygienic standards of the device but also reduces health risks and maintenance costs for patients during use. A foamless design not only eliminates the risk of blockages that foam in traditional gas passages might cause but also ensures continuity and consistency of the gas passage, further optimizing aerodynamic performance. A foamless gas passage system provides greater flexibility and diversity in the overall design of the device. Beyond traditional foam materials, options like silicone and rubber can be used for other high-performance damping and sound insulation materials to meet specific needs of different patients and application scenarios. This diversified material selection not only enhances the adaptability and compatibility of the device but also broadens its application prospects. c. The foamless design also helps to ensure that the device maintains high levels of performance and quality standards after multiple uses. For example, traditional foam may degrade, deform, or cause blockages over time, or lead to overheating, short-circuiting, or mechanical damage to the device. These issues can pose safety risks and affect the device's performance, but a foamless design eliminates these potential problems, making the device more durable, maintaining efficient operation, and extending its lifespan. Thus, the lifespan of foam is typically more limited compared to other components within the gas passage, so removing foam from the gas passage, on one hand, extends its lifespan. d. This disclosure, with its highly efficient internal noise reduction structures and components, can achieve equivalent noise reduction effects even without foam. However, for some patients, noise reduction might be a more critical factor. Therefore, under the premise of ensuring safety and basic functionality, for patients with stringent noise requirements, the addition of foam can be considered to achieve higher quality noise reduction effects. Devices can be customized based on individual needs; options include adding foam in the device to further reduce noise, as designs with foam can offer superior noise reduction capabilities. In summary, the design of the gas passage considers multiple factors, including noise control, environmental impact, safety, and cost-effectiveness. Whatever the patient's needs, this design provides flexible options to meet various usage scenarios and preferences.

3. From the supplier's perspective, this disclosure reduces costs in multiple aspects and is more economical. Additionally, the foamless interior of the gas passage is environmentally friendly. a. The foamless design strategy inside the gas passage can reduce the costs of material procurement and manufacturing of the device. Since the airflow does not pass through foam, by expanding the range of foam choices and reducing the amount of foam used, production efficiency can be effectively improved, lowering production costs and thereby bringing higher economic benefits. This not only helps enhance the product's market competitiveness but also enables it to gain a larger market share and customer trust in an increasingly competitive market environment. b. The ventilation component of this disclosure is in the form of a single basic body, simpler than existing noise reduction components on the market and made from a single material, making it more economical in terms of material and manufacturing costs. Moreover, due to the simplicity and efficiency of the noise reduction components, the gas passage interior does not require additional complex structures to achieve the desired noise reduction effects with the ventilation component alone. In the absence of foam, the gas passage also eliminates the need for extra structures to secure the foam. Overall, the interior of the gas passage in this disclosure is more streamlined and simpler than existing designs on the market, making it easier to manufacture. From a manufacturer's perspective, both foamless and foam-inclusive modular designs have their advantages. Furthermore, because the foamless design does not need to account for foam degradation or moisture issues over prolonged use, the requirements for storage and transportation are also simpler and more flexible. Environmental concerns are paramount in modern manufacturing, and a foamless gas passage aligns with internationally advocated environmental principles. A foamless gas passage reduces the consumption of limited resources and lessens the environmental impact during the production process.

DETAILED DESCRIPTION

Figure 1:
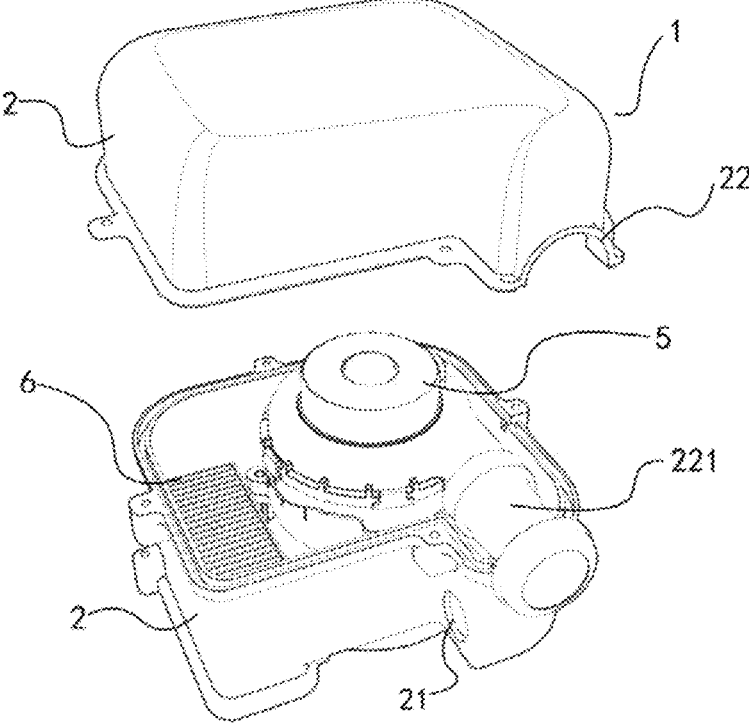
FIG. 1 is a three-dimensional schematic diagram of a form of a gas passage according to an embodiment of the present disclosure.
Figure 2:
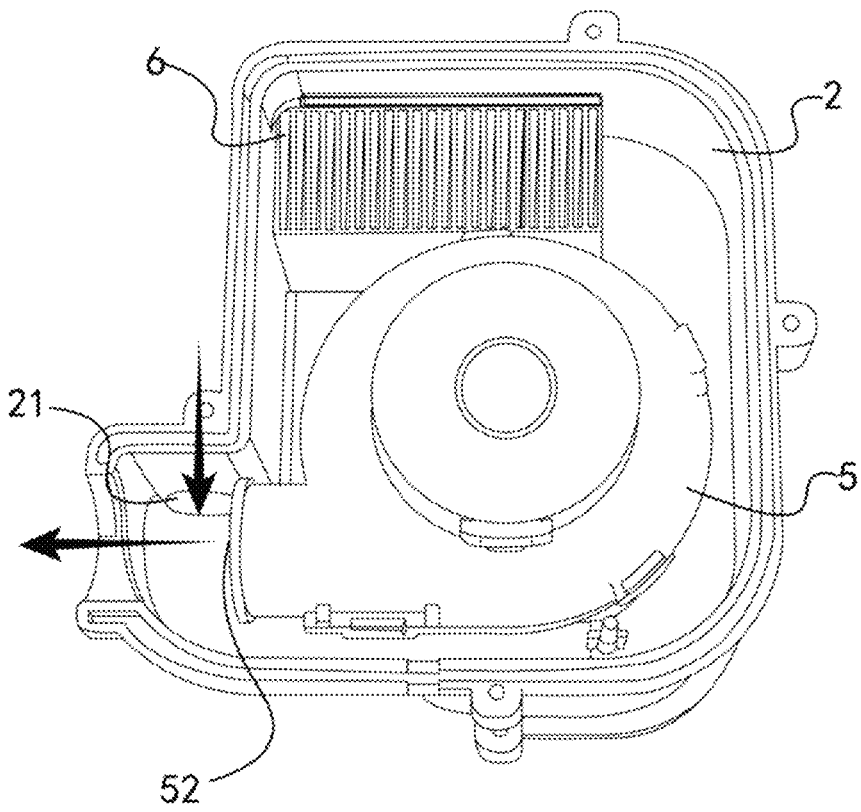
FIG. 2 is a structural layout schematic diagram of another form of a gas passage according to an embodiment of the present disclosure.
Figure 3:
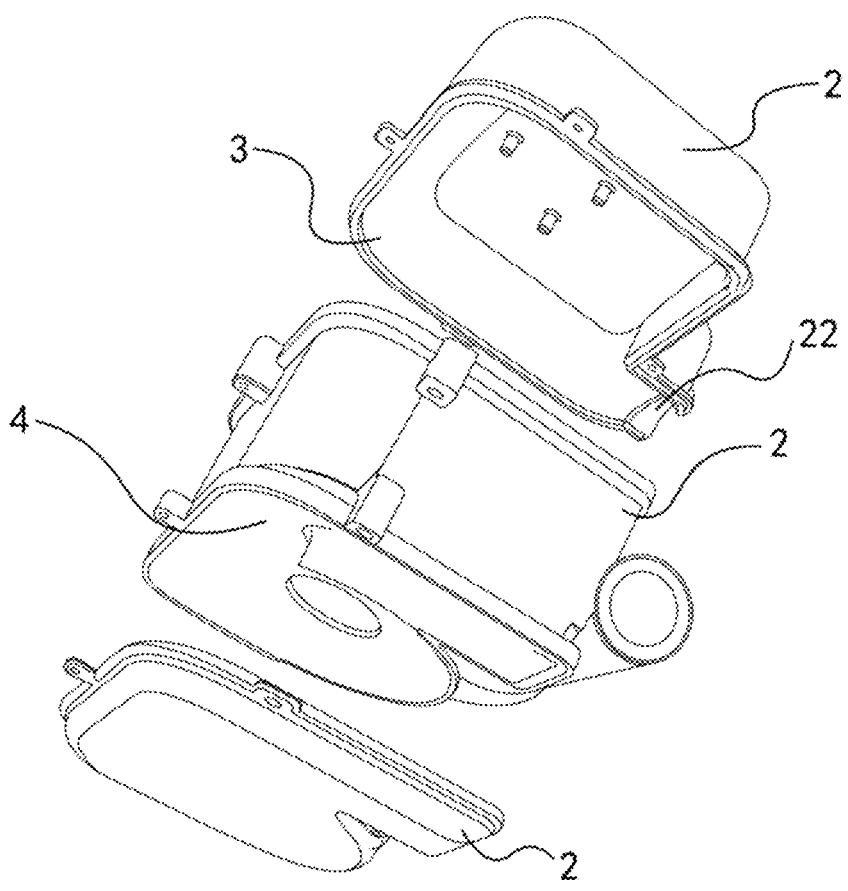
FIG. 3 is a schematic diagram of a form of the casing of a gas passage according to an embodiment of the present disclosure.

To facilitate understanding of the disclosure described herein, a more comprehensive description will be provided with reference to the accompanying drawings. The drawings illustrate typical embodiments of the disclosure. However, the disclosure can be implemented in many different forms and is not limited to the embodiments described herein. Instead, these embodiments are provided to ensure a thorough and comprehensive disclosure of the disclosure.

Unless otherwise defined, all technical and scientific terms used herein have the same meaning as commonly understood by those of ordinary skill in the art to which this disclosure belongs. The terminology used in the description of the disclosure herein is for the purpose of describing particular embodiments only and is not intended to be limiting of the disclosure.

This disclosure scientifically tests and treats the structure within the gas passage and the coordination between its components, maximizing the advantages of the internal component structures. This enhances the performance and efficiency of the entire respiratory-related device, achieving superior states of noise reduction, efficiency, reliability, and lifespan. Therefore, the gas passage of this disclosure not only enhances the performance metrics of respiratory-related devices but also provides patients with a more stable, safer, and more comfortable user experience, demonstrating a clear competitive market advantage. This represents a superior technological disclosure for patients, producers, and the market alike.

Below are specific embodiments illustrating several structures of a gas passage used in a PAP device according to this disclosure.

Embodiment 1

This embodiment provides a gas passage 1 used in a PAP device. This embodiment includes a three-dimensional schematic diagram, a structural breakdown diagram, airflow path diagrams, structural data illustrations, and schematic diagrams of the ventilation component 6 and its integration with the gas passage 1, as referenced in FIGS. 1-17. This embodiment involves a gas passage 1 specifically configured to improve the respiratory system and address disorders such as sleep apnea, particularly when used within a PAP device. The design of gas passage 1 and its components not only provides an effective airflow channel but also reduces noise and enhances patient comfort. This gas passage 1 includes a casing, at least two chambers formed within the casing, a blower 5 positioned within one of the chambers, and a noise-reducing ventilation component 6 within the gas passage 1.

Specifically, the gas passage 1 includes a casing 2, which is composed of two or more parts that together form a complete casing 2, configured to enclose and accommodate internal components (i.e., all components within the casing 2, including a blower 5, ventilation component 6, etc.), providing protection for these components and ensuring they are not affected by external conditions and that the gas passage 1 operates stably. The casing 2 of the passage has at least one air intake 21 and at least one air outlet 22; the air intake 21 allows external air to enter the casing 2 of the passage to be pressurized by the blower 5, and the air outlet 22 connects to an opening on the casing to connect a respiratory hose and the blower 5, enabling the pressurized air from the blower 5 to be delivered to the patient's airway. Inside the casing, there is a noise reduction system; when the gas passage 1 is operational, the parts of the casing 2 tightly combine to form a relatively sealed environment. This relatively sealed design ensures that airflow within the casing 2 of the gas passage 1 can flow in a controlled environment, providing a clear, unobstructed flow path. In one instance, since the noise produced by the air intake 21 is often the loudest in the entire device, to effectively reduce this noise, the air intake 21 and air outlet 22 are provided on different planes. Such a design helps reduce noise overlap, thus providing a quieter user experience. Additionally, the heights of the air intake 21 and the air outlet 22 are not the same, this setup helps to further increase the vertical distance between the air intake 21 and air outlet 22, further reducing noise. The casing 2 of the gas passage 1 is made from one of the following materials: polypropylene (PP), polycarbonate (PC), polyethylene terephthalate-1,4-cyclohexane dimethanol ester (PCTG), polyamide (PA), or polyetheretherketone (PEEK).

Figure 4:
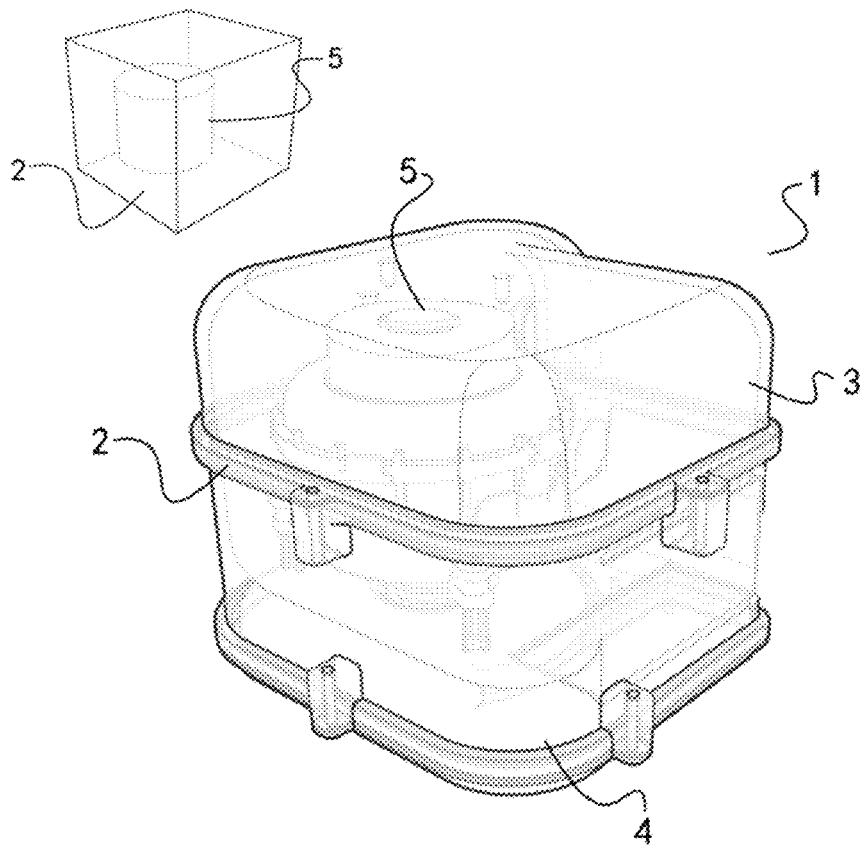
FIG. 4 is a schematic diagram illustrating the volume ratio of a blower to the chamber where the blower is provided in a form of a gas passage according to an embodiment of the present disclosure.

When the gas passage 1 operates, the internal space of the casing 2 of the gas passage 1 is divided into a combination of multiple smaller spaces, meaning the casing 2 of the gas passage 1 is divided into at least two chambers configured to provide space for gas flow and accumulation. One of these chambers provides space for placing the blower 5, ensuring that the volume of the chamber housing the blower is at least three times the volume of the blower 5 (as shown in FIG. 4). In one scenario, the internal chambers include at least a first chamber 3 and a second chamber 4. The blower 5 may be located in the first chamber 3, allowing gas to first enter and be pressurized by the blower 5 in the first chamber 3, and then the pressurized gas flows into the second chamber 4, making the gas pressure in the second chamber 4 higher than in the first chamber 3. Alternatively, the blower 5 could also be located in the second chamber 4.

Figure 5:
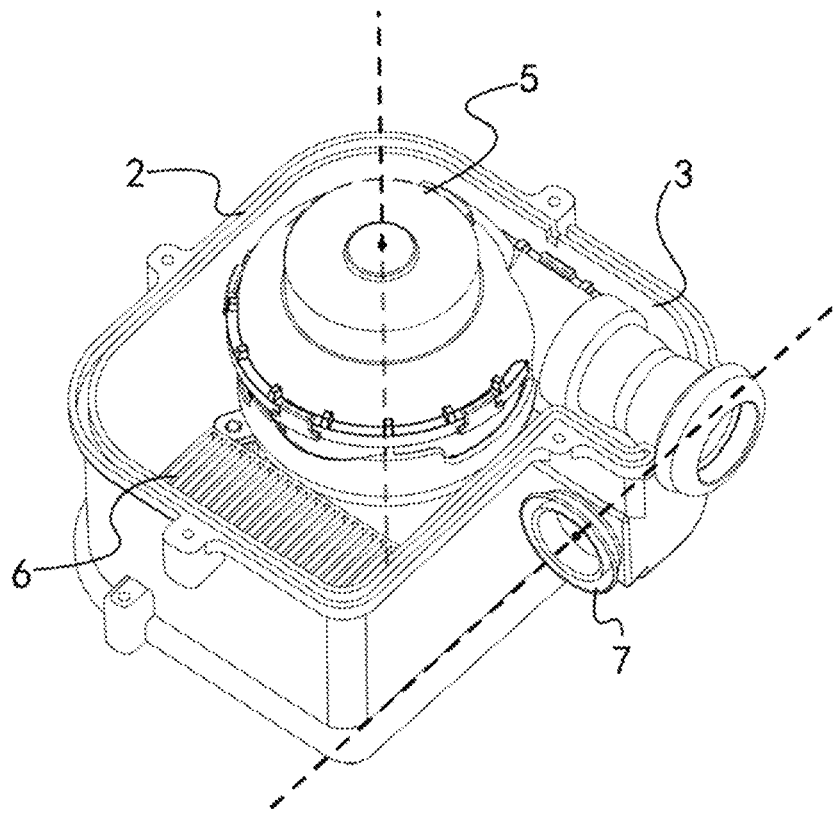
FIG. 5 is a schematic diagram showing that the axis of the air intake of a gas passage's casing and the axis of the blower's inlet are not parallel, according to an embodiment of the present disclosure.
Figure 6:
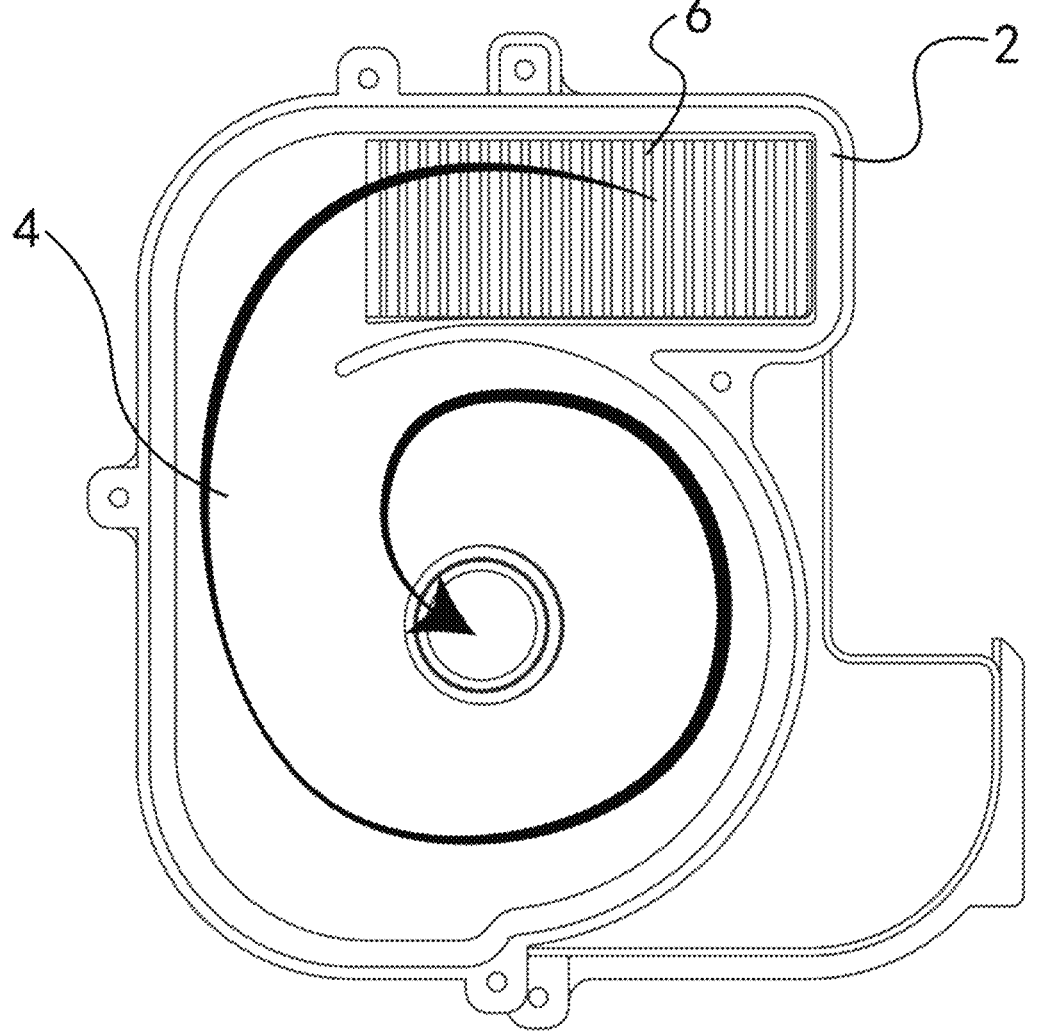
FIG. 6 is a schematic diagram of the main airflow path in the second chamber of a form of a gas passage according to an embodiment of the present disclosure.
Figure 7:
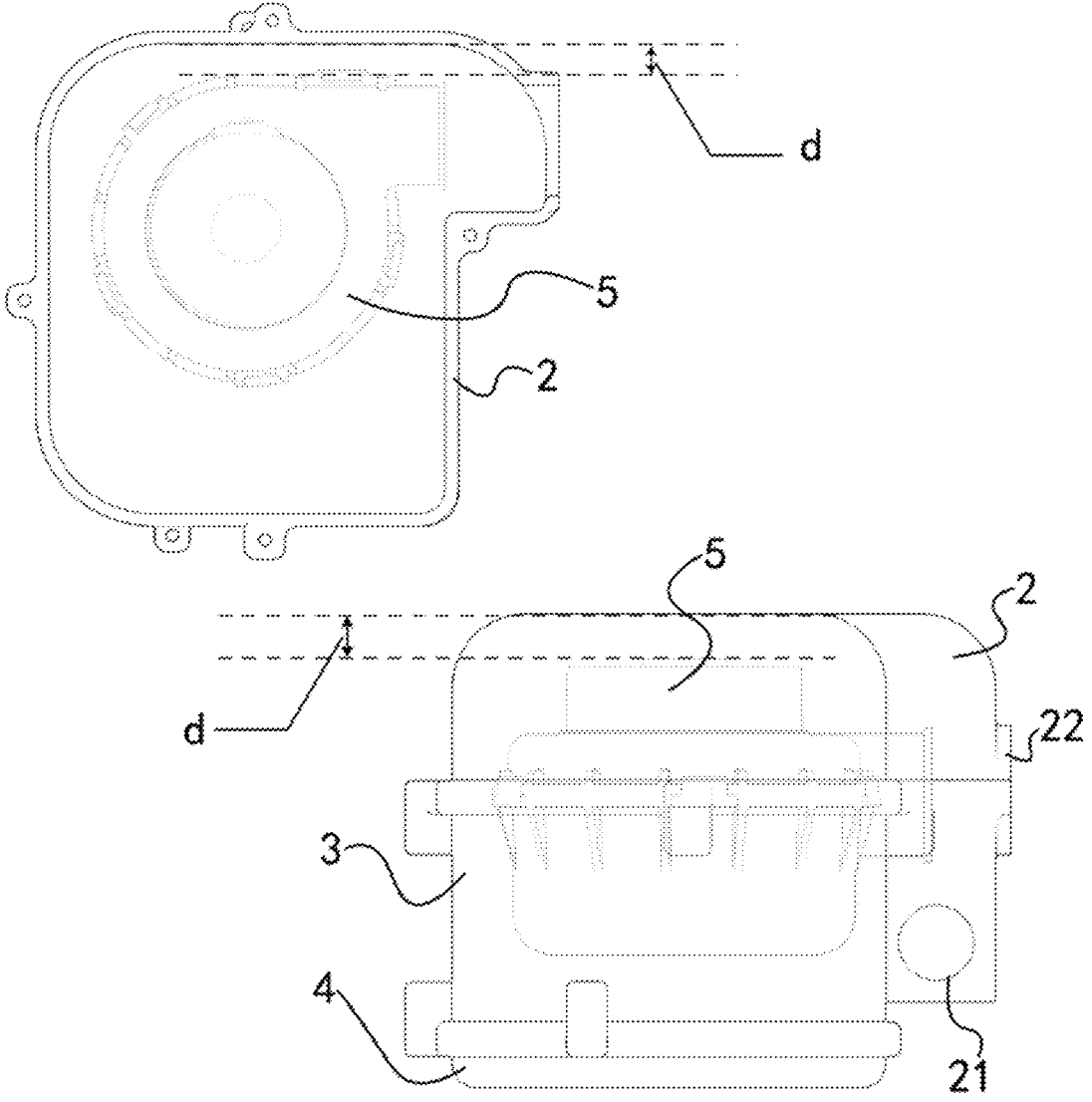
FIG. 7 is a placement schematic diagram of the blower in a form of a gas passage according to an embodiment of the present disclosure.

The blower 5, located within a chamber, has an inlet 51 to receive incoming gas and an outlet 52 to allow gas to flow out. In one implementation, the inlet 51 of the blower 5 communicates with other chambers not housing the blower 5, creating a scenario where the gas pressure in the first chamber 3 is higher than in the second chamber 4. In another implementation, the axial line of the air intake 21 on the casing 2 of the passage 1 is not parallel to the axial line of the inlet 51 of the blower 5 (as shown in FIG. 5). To stabilize the airflow within the gas passage 1 and reduce noise, the configuration of the chamber communicating with the inlet 51 of the blower 5 (such as the second chamber 4) is specified, i.e., designing the second chamber 4 so that the airflow enters the inlet 51 of the blower 5 either in a straight manner (along the axis direction at the inlet 51 of the blower 5) or in alignment with the rotation direction of the blower 5 (the direction of the blower impeller rotation) (as shown in FIG. 6). When the blower 5 is positioned in the middle of its chamber, with the inlet 51 of the blower 5 at the central part of the chamber wall, this setup allows the airflow to enter the blower 5 more uniformly from the chamber, ensuring the airflow toward the blower 5 avoids excessive turbulence and eddies, thus reducing noise and instability caused by uneven airflow. In this disclosure, the blower 5 is configured to be at least 4 mm away from the inner wall of the casing 2 of the passage 1 (as shown in FIG. 7, where d≥4 mm), to provide space for airflow movement and effectively isolate vibrations from the blower 5.

Figure 8:
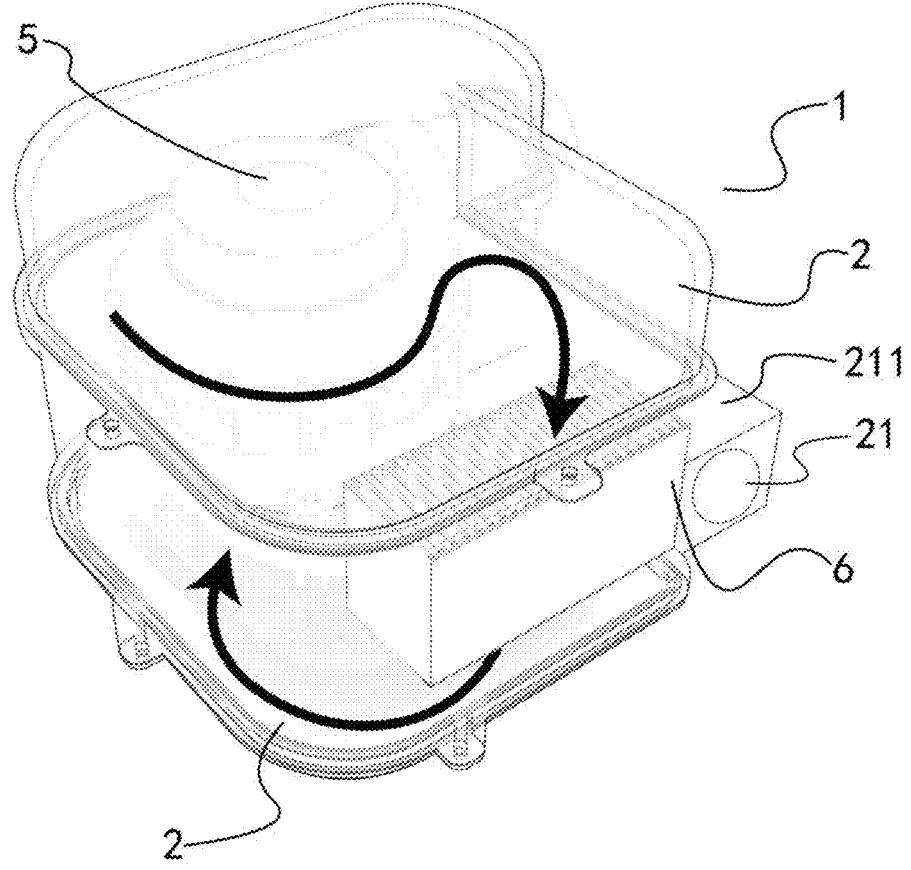
FIG. 8 is a schematic diagram showing the ventilation component connecting the first and second chambers in a form of a gas passage according to an embodiment of the present disclosure.
Figure 9:
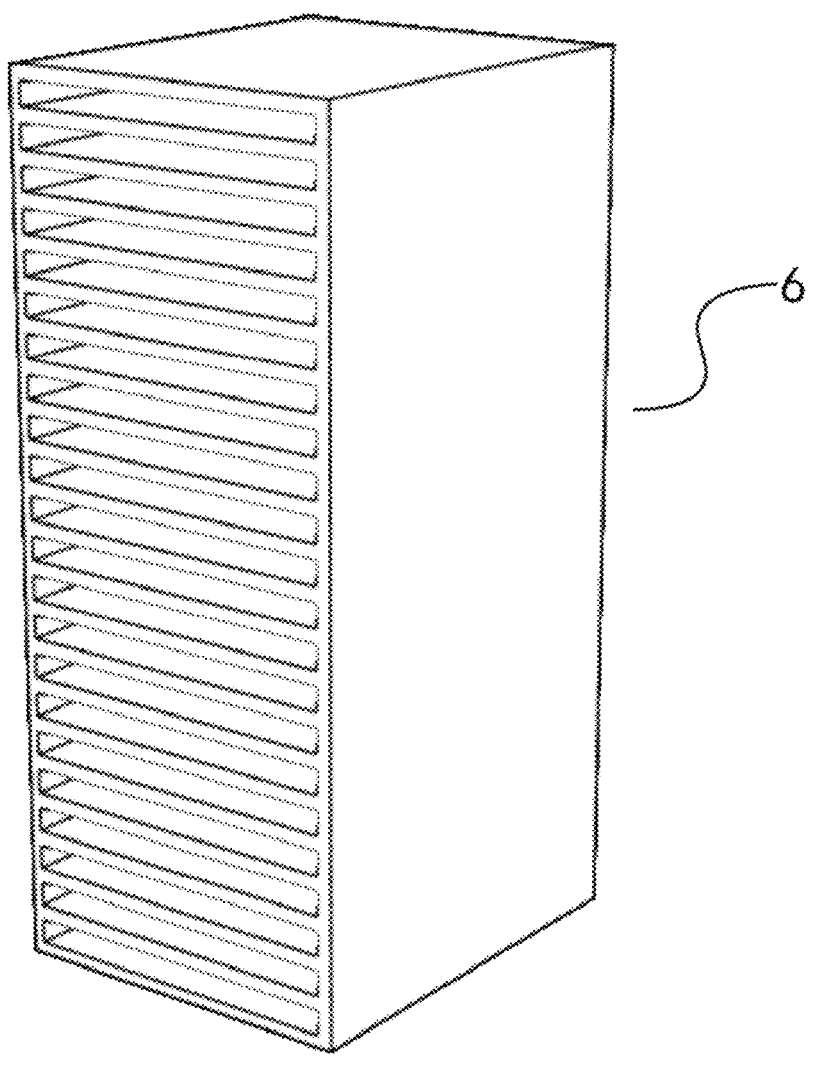
FIG. 9 is a structural schematic diagram of the ventilation component in a form of a gas passage according to an embodiment of the present disclosure.
Figure 10:
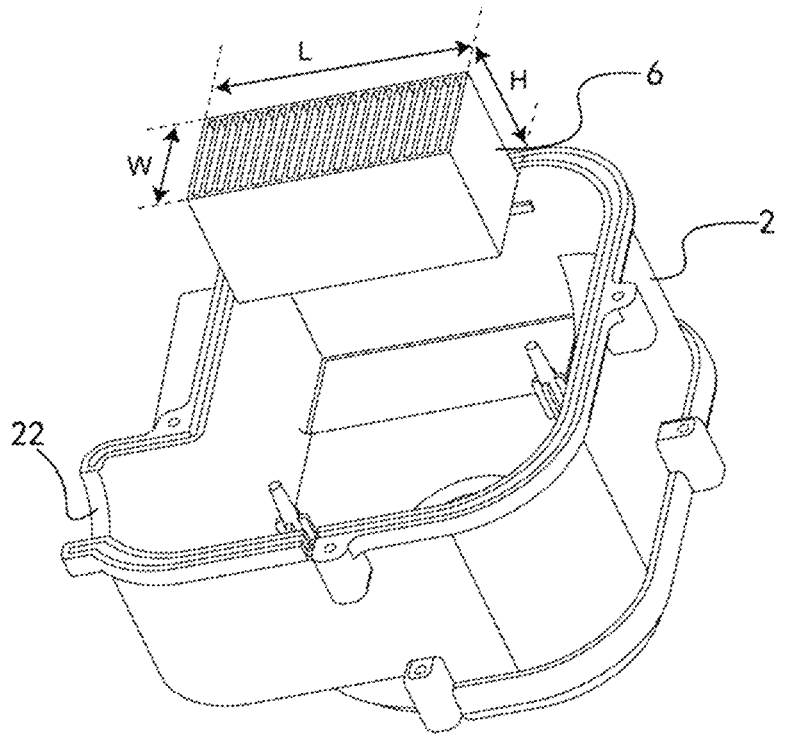
FIG. 10 is a schematic diagram indicating the length, width, and height of the ventilation component in a form of a gas passage according to an embodiment of the present disclosure.
Figure 11:
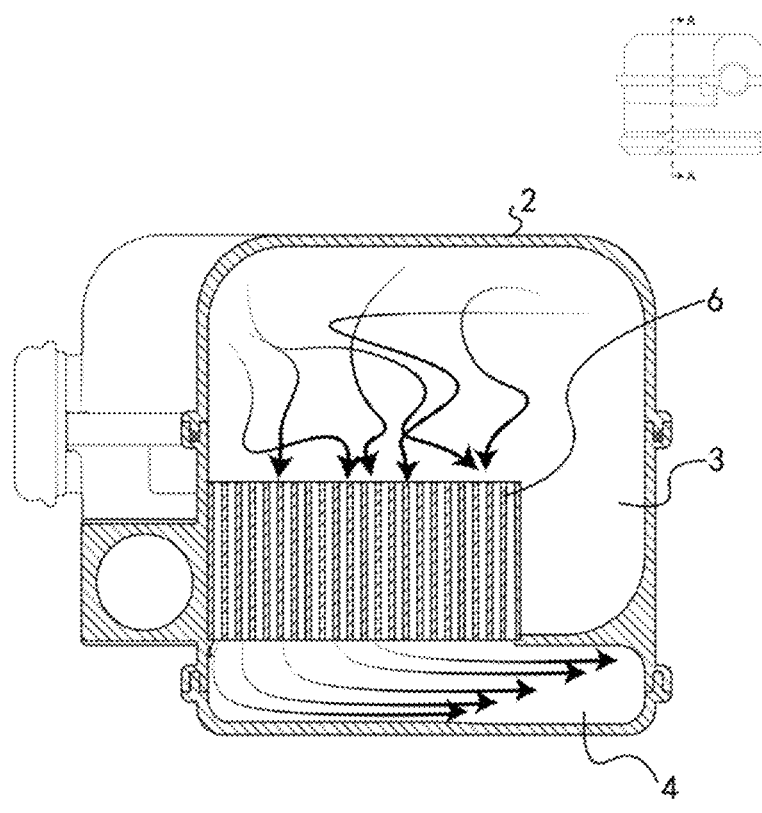
FIG. 11 is a schematic diagram illustrating the noise reduction by a single ventilation component in a gas passage according to an embodiment of the present disclosure.
Figures 12A, 12B, 12C, 12D, 12E, 12F:
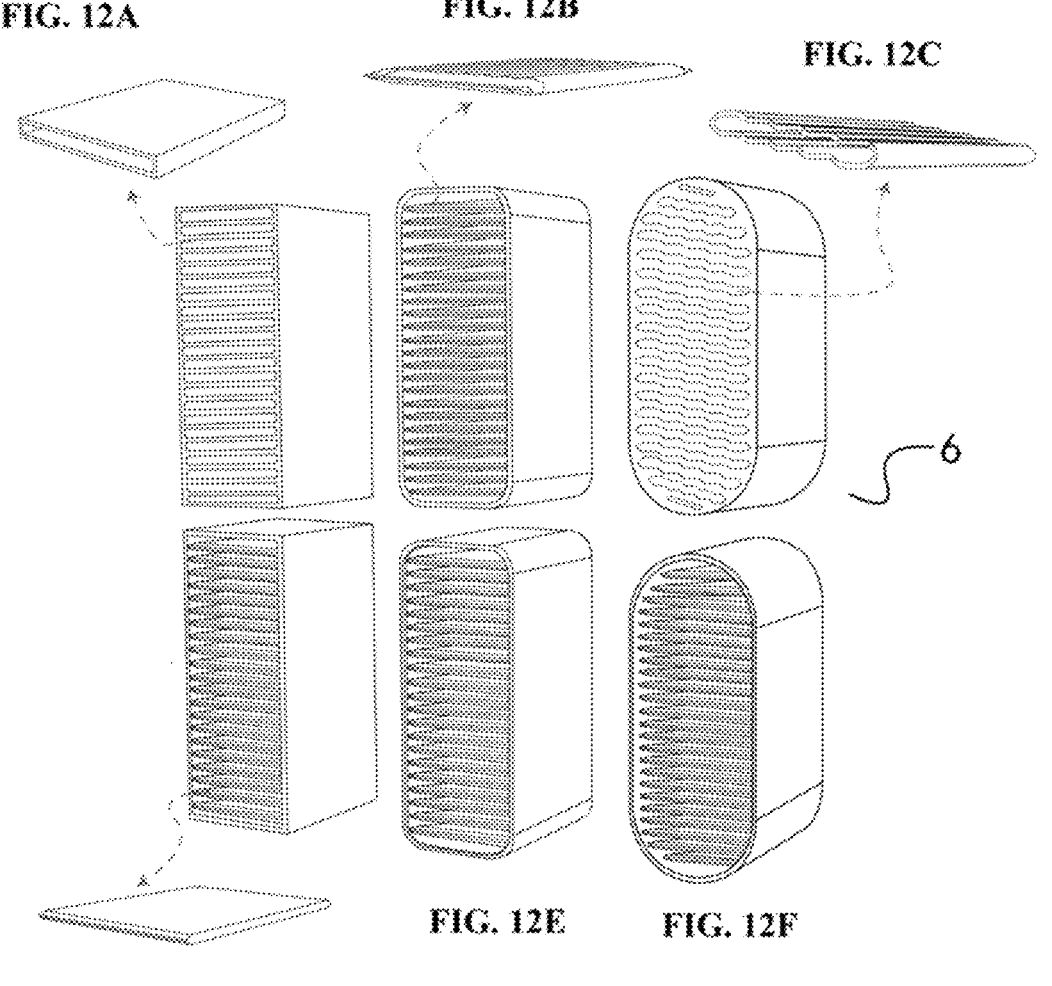
FIGS. 12A, 12B, 12C, 12D, 12E, and 12F are schematic diagrams of different forms of ventilation components in a form of a gas passage according to an embodiment of the present disclosure.
Figure 13:
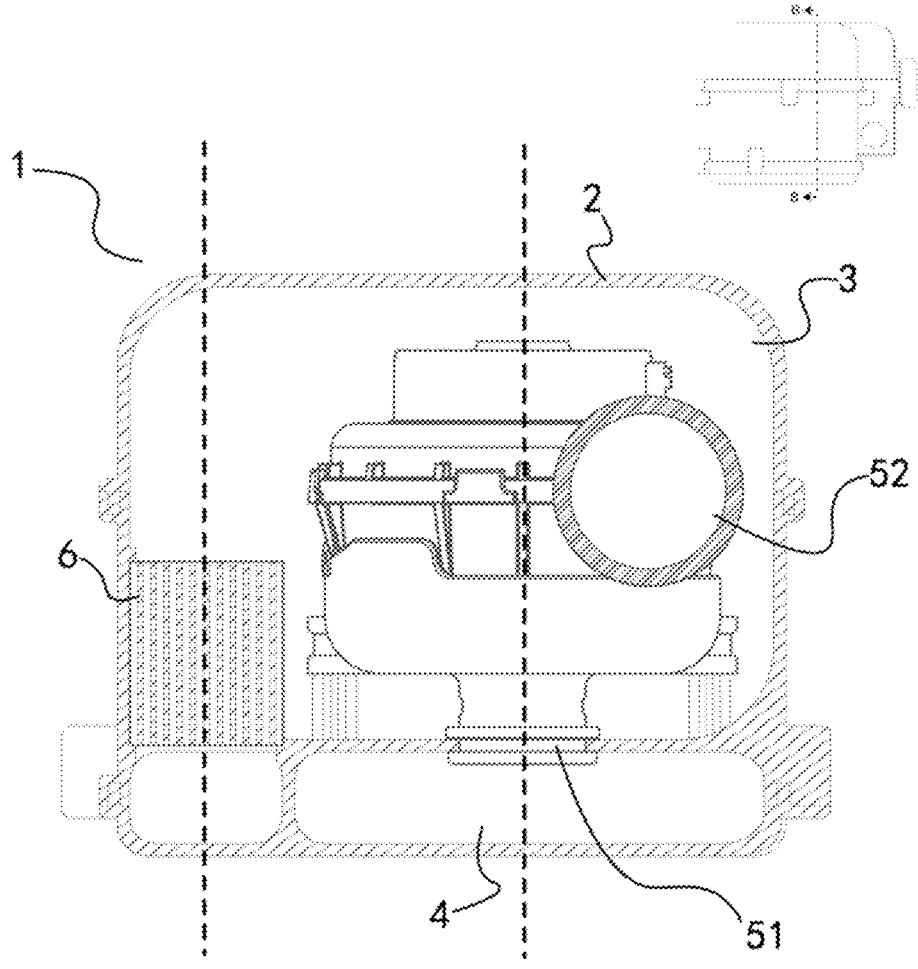
FIG. 13 is a schematic diagram showing the direction of gas passing through the ventilation component parallel to the blower in a form of a gas passage according to an embodiment of the present disclosure.
Figure 14:
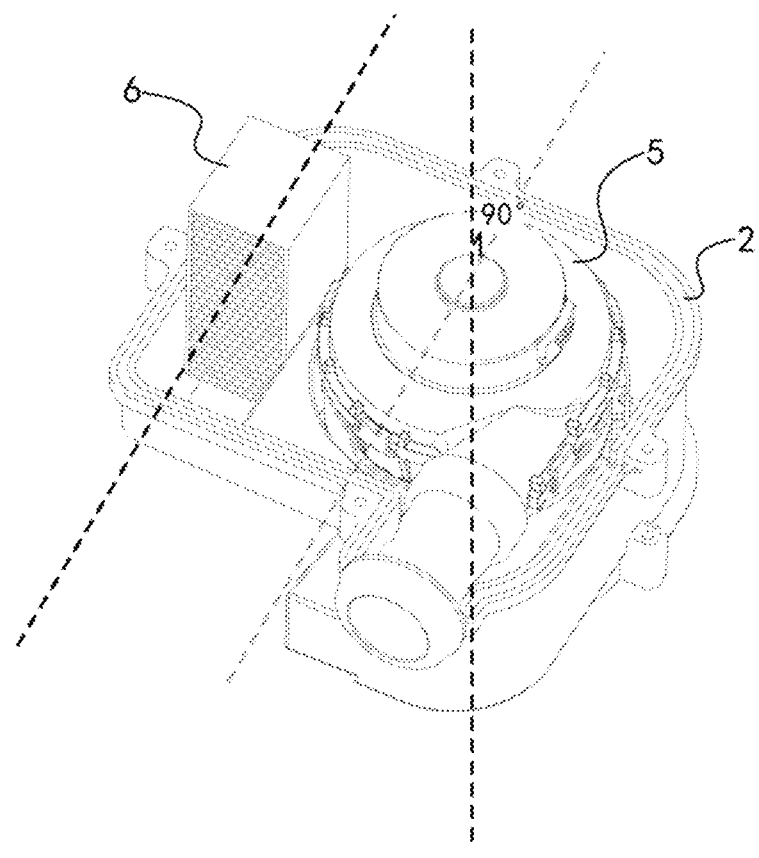
FIG. 14 is a schematic diagram showing the direction of gas passing through the ventilation component perpendicular to the blower in a form of a gas passage according to an embodiment of the present disclosure.
Figure 15:
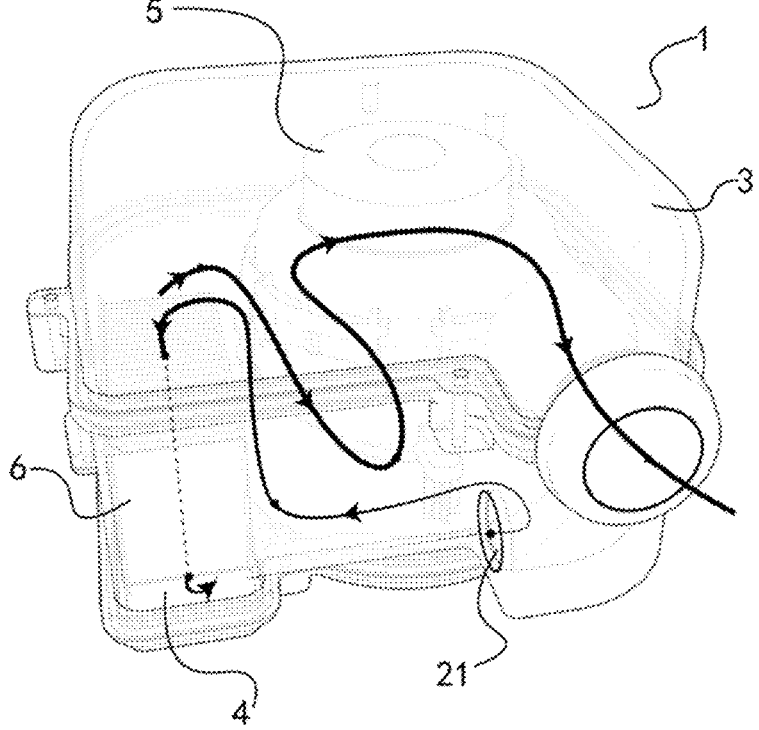
FIG. 15 is a schematic diagram of the main airflow path in a form of a gas passage according to an embodiment of the present disclosure.
Figure 16:
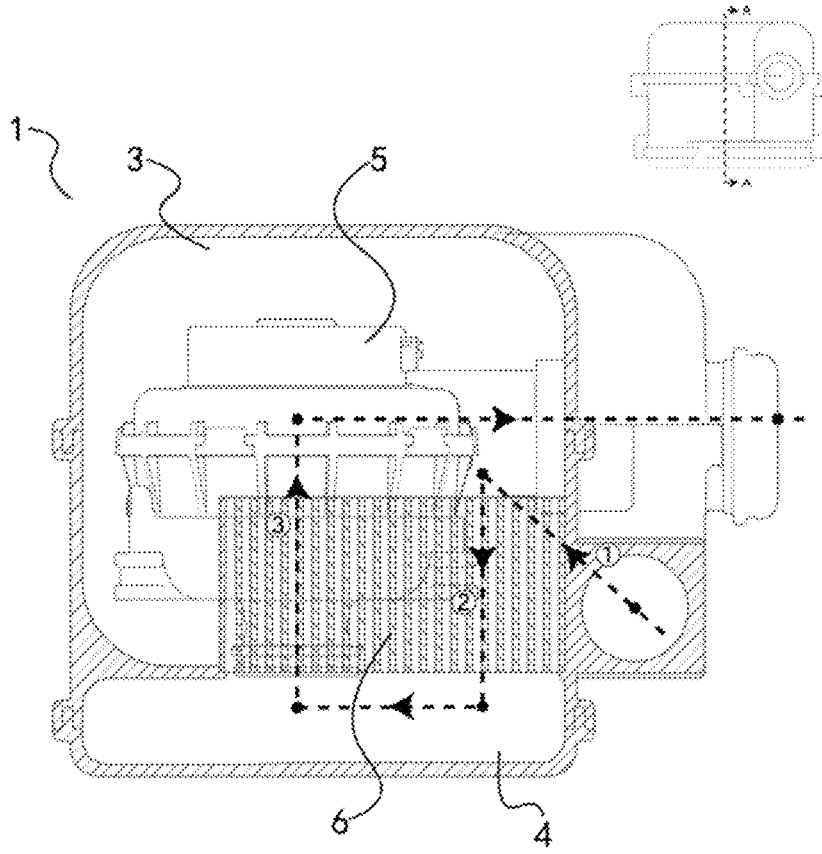
FIG. 16 is a schematic diagram showing the formation of three height differences in the airflow within a form of a gas passage, according to an embodiment of the present disclosure.
Figure 17:
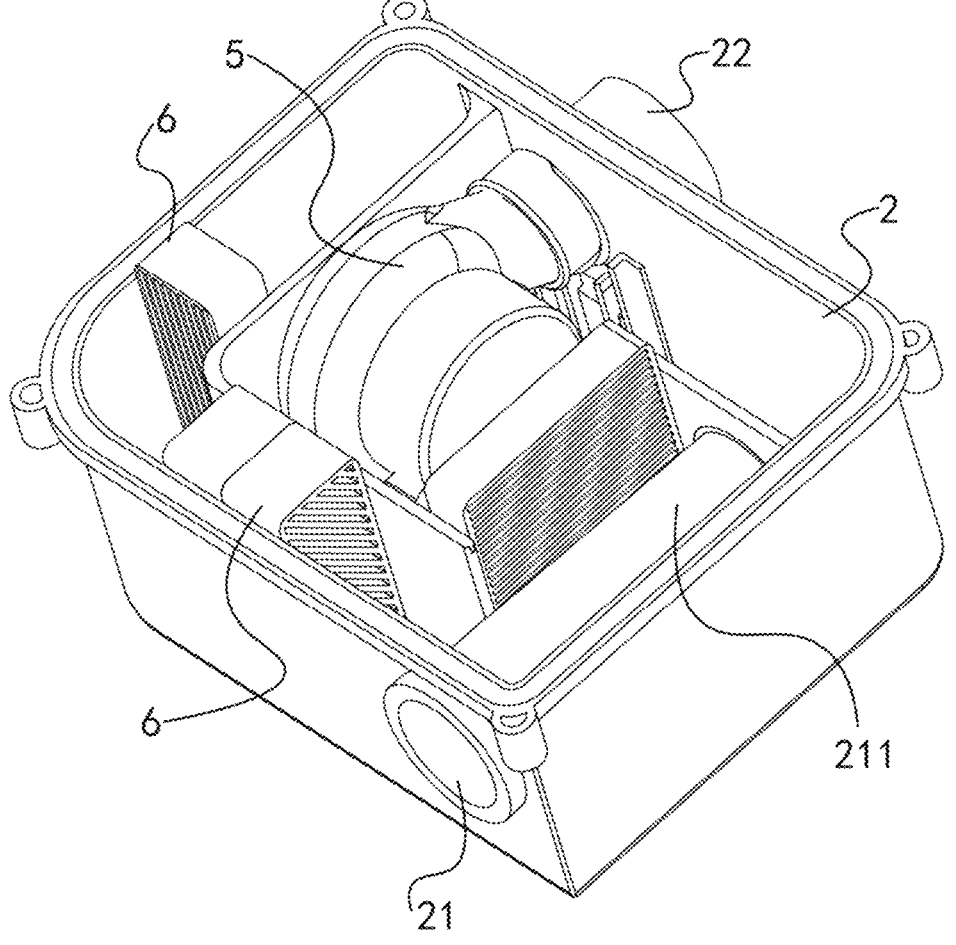
FIG. 17 is a schematic diagram illustrating noise reduction by multiple ventilation components combined in a form of a gas passage according to an embodiment of the present disclosure.

The ventilation component 6 is configured to connect chambers, enabling gas to flow through it within the chambers (as shown in FIG. 8). The ventilation component 6 has an inlet end and an outlet end for the entry and exit of gas, surrounded by a peripheral wall and multiple baffles forming the complete ventilation component 6, with both ends distanced at least 3.45 mm from the inner wall on the casing 2 of the gas passage 1. The design of the ventilation component 6 not only considers its structural durability but also its functionality. It effectively segments large-scale airflow, reducing noise produced during airflow and allowing for smoother passage through the gas passage 1. Specifically, its internal structure includes baffles spaced at certain intervals, where the spacings between the baffles form multiple channels for gas flow. That is, the ventilation component 6 includes spacings that allow gas to pass through (as shown in FIG. 9), with a spacing between each of the baffles being between 0.8 mm to 2.2 mm, optimally 1.2 mm to 2 mm. This arrangement of multiple gaps splits larger airflows into smaller, more uniform streams (as shown in FIG. 11). The baffles are core structural components inside the ventilation component 6 that can take various forms; the baffles inside ventilation component 6 may be horizontal strips parallel to the horizontal plane, vertical strips perpendicular to the horizontal plane, or at any other angle. The primary function of these baffles is to segment the airflow and form channels for gas flow. Therefore, the end of the ventilation component 6 where the gas enters can be configured to include angled tips to better segment the airflow that is about to enter the ventilation component 6. Additionally, the baffles may vary in thickness (as shown in FIGS. 12A, 12B, 12C, 12D, 12E, and 12F), where in one implementation, the baffles of the ventilation component 6 have a tapered trapezoidal shape. This design causes the gas to flow through the channels in a complementary trapezoidal shape, which accelerates the airflow as it passes through ventilation component 6, resulting in further noise reduction in some cases. The peripheral shape of the ventilation component 6 can be square, circular, trapezoidal, or any other suitable shape. In this embodiment, the casing 2 of the gas passage 1 has an inner wall, and the ventilation component 6 is located within one of the chambers, with its first end allowing gas entry and the second end allowing gas exit. Both ends (the inlet end and the outlet end) are at least 5 mm away from the inner wall on the casing 2 of the gas passage 1. Furthermore, the height of the ventilation component 6 is set to be at least 10 mm, and the length-to-width ratio ranges of 0.1 to 1, with an optimal length-to-width ratio range of 0.3 to 0.55. These parameters are selected to achieve optimal airflow distribution, ensuring stable gas flow within the chambers. This height range ensures that after passing through the ventilation component 6, the gas has sufficient space and time to maintain its segmented state, preventing the airflow from recombining too quickly. This elongated design also helps reduce pressure loss in gas flow and provides a more uniform distribution of gas. The length-to-width ratio range ensures that the gaps between the baffles are neither too narrow nor too wide to be ineffective at noise reduction. In one implementation, the ventilation component 6 includes baffles configured with inclined surfaces (each baffle is angled relative to the horizontal plane), configured to effectively separate the airflow and reduce the noise transmission at the inlet 51 of the blower 5. This design allows the airflow to move in a unidirectional manner, preventing backflow and enabling more effective noise reduction in some cases. Additionally, the ventilation component 6 and the blower 5 are positioned within the gas passage 1 such that the direction of gas passing through the ventilation component 6 is parallel or perpendicular to the direction of gas entering the blower 5 (as shown in FIGS. 13 and 14). When the ventilation component 6 is placed inside the gas passage 1, the passage 1 utilizes the ventilation component 6 and its internal structure for noise reduction. The gas flows from the air intake 21 on the casing 2 of the gas passage 1 to the air outlet 22, forming a primary flow path (as shown in FIG. 15). During the operation of the gas passage, the majority of the gas flows along a prescribed path determined by the internal structure and arrangement of components within the gas passage. This path is referred to as the primary flow path. Experiments and data have shown that the longer this path, the better the noise reduction effect, with the primary flow path being at least 160 mm in length. In this embodiment, the path has height differences, with at least three such differences in one implementation (as shown in FIG. 16). The multiple height differences effectively elongate the length of the gas passage 1, providing not only a horizontal airflow path but also increasing the vertical airflow path. The overlay of horizontal and vertical airflow paths gives the gas passage 1 of this disclosure a longer and more convoluted airflow path compared to existing market options. Therefore, in this respect, the structure of the disclosure described herein achieves greater noise reduction compared to existing gas passages on the market. Furthermore, the methods of noise reduction by the ventilation component 6 within the gas passage 1 can take multiple forms. The ventilation component 6 can be used individually within the gas passage 1 or in a configuration where multiple ventilation components 6 are combined within the gas passage 1 to reduce noise. When multiple ventilation components 6 are used in combination, they can be spaced apart or tightly adjoined without gaps (as shown in FIG. 17).

In another implementation, the ventilation component 6 is integrally formed with the casing 2 of the gas passage 1.

Figure 18:
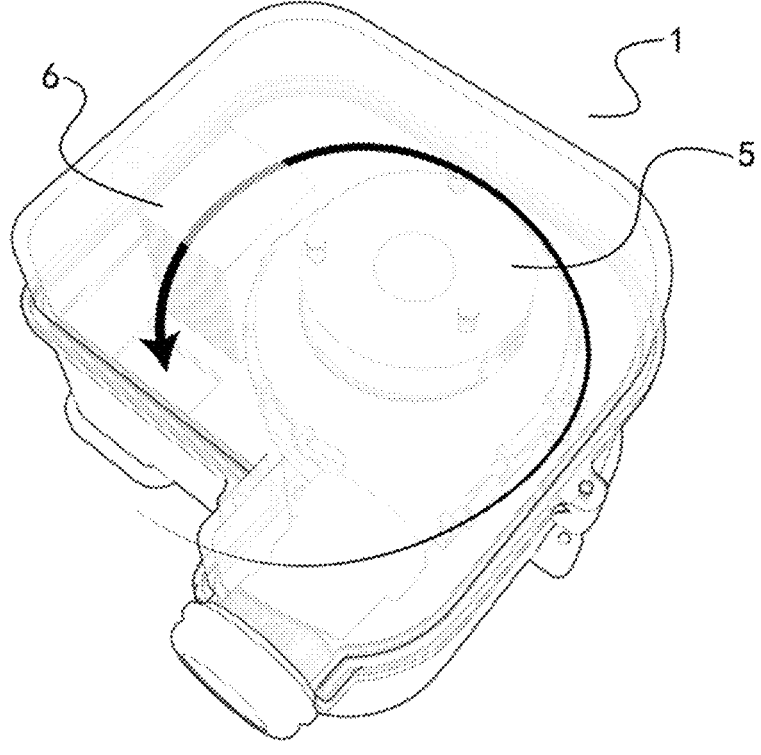
FIG. 18 is a schematic diagram of the placement of the ventilation component within a form of a gas passage according to an embodiment of the present disclosure.

In another implementation, the ventilation component 6 is located within the gas passage 1 but does not connect the first chamber 3 and the second chamber 4 (i.e., the ventilation component 6 is situated within a separate chamber, as shown in FIG. 18).

Figure 19:
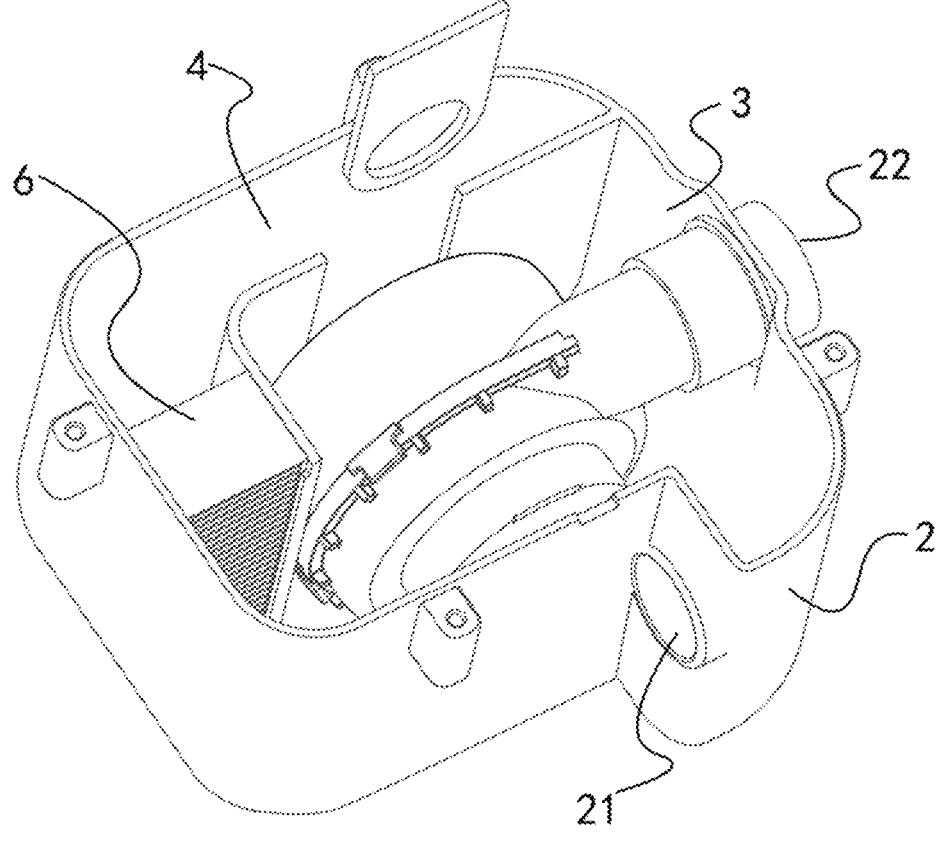
FIG. 19 is a schematic diagram showing the division of chambers in another form of a gas passage according to an embodiment of the present disclosure.

In another implementation, the gas passage 1 has a different form of chamber division than the ones described in the previous implementations (as shown in FIG. 19).

Embodiment 2

Figure 20:
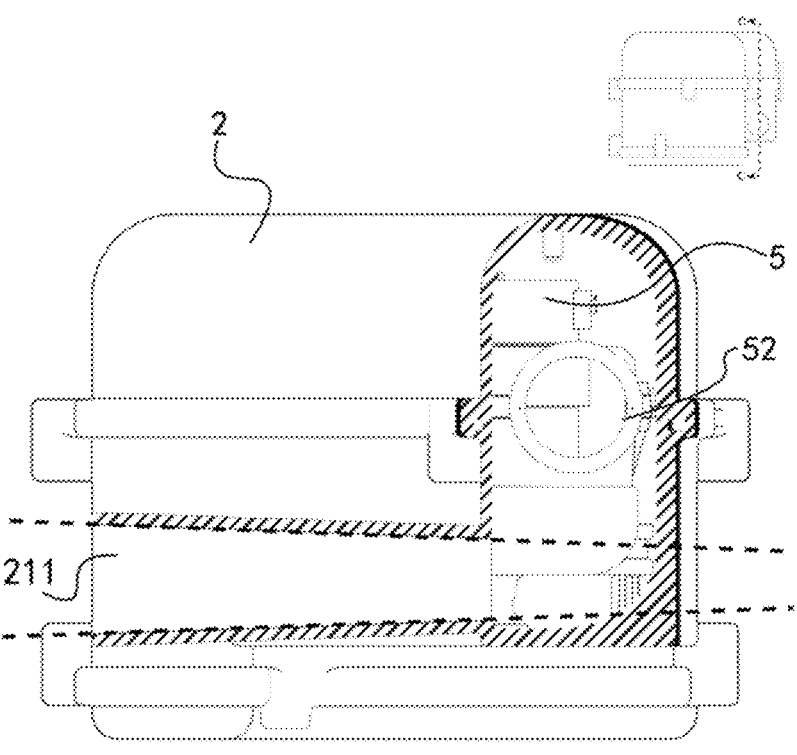
FIG. 20 is a sectional diagram of a gas passage with a tapered intake pipe according to an embodiment of the present disclosure.
Figures 21A, 21B:
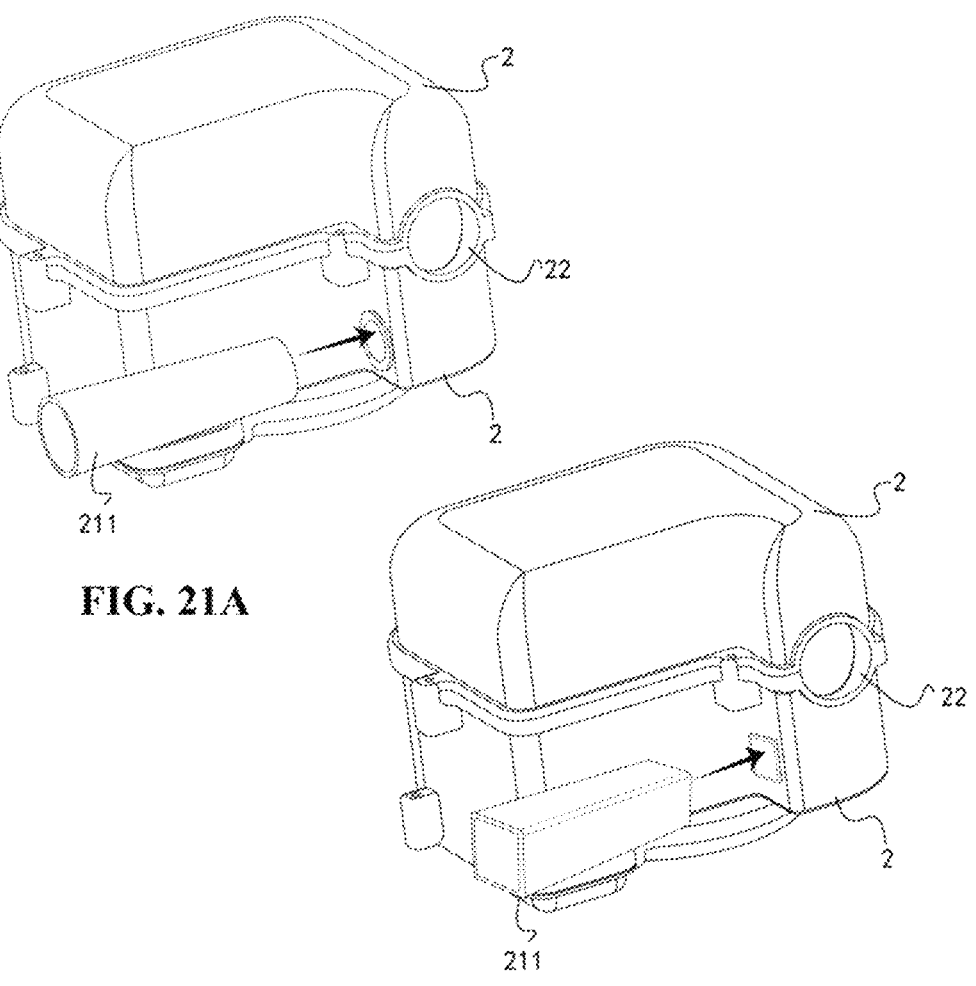
FIGS. 21A and 21B are schematic diagrams of a gas passage with different forms of non-integrated intake pipes and a casing according to an embodiment of the present disclosure.
Figure 22:
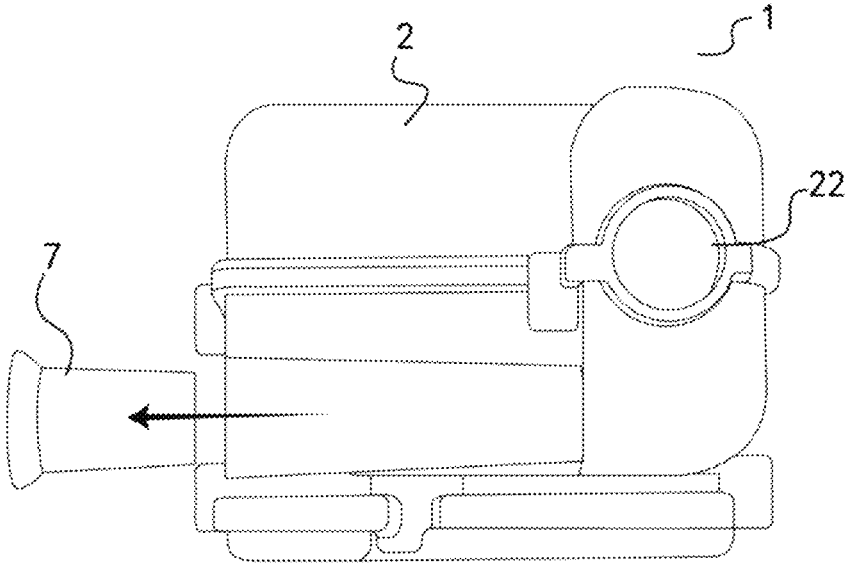
FIG. 22 is a schematic diagram of a form of a gas passage with a flexible component according to an embodiment of the present disclosure.

This embodiment provides a gas passage 1 used in a PAP device, as referenced in FIGS. 20-22. This embodiment includes side views and cross-sectional diagrams of the gas passage 1. In the embodiment shown in FIGS. 20-22, which differs from the gas passage 1 in Embodiment 1, the casing 2 of the gas passage 1 includes an intake pipe 211 connected to an air intake 21. The intake pipe 211 is configured to connect the external environment to the interior of the casing 2 of the gas passage 1, while the air outlet 22 is connected to an exhaust pipe 221, configured to receive the pressurized gas flowing out from the outlet 52 of the blower 5. The intake pipe 211 includes a channel of a certain length, ranging from 25 mm to 80 mm, typically a cylindrical channel, but it can also be square or any other shaped channel. When the intake pipe 211 has a draft angle (as shown in FIG. 20), an intake pipe 211 with a certain taper can accelerate the airflow, reducing the noise as the airflow enters the internal chambers through the intake pipe 211. This improved design of the gas passage 1 might be a significant advantage for those who are particularly sensitive to noise or need to sleep in a quiet environment. Tests have concluded that a smaller taper in the intake pipe 211 does not significantly affect the airflow; hence, this disclosure specifies that the taper of the intake pipe 211 should be at least 0.1°.

The intake pipe 211 has ports for gas entry and gas exit. When the intake pipe 211 is connected to the air intake 21 on the casing 2 of the gas passage 1, the intake end of the intake pipe 211, positioned outside the casing 2 of the gas passage 1, replaces the casing 2's air intake 21 and becomes the first entry for gas flowing into the gas passage 1. The outlet end of intake pipe 211 is located inside the gas passage 1, allowing gas to enter the chamber within the gas passage 1. Since the internal chamber of the gas passage 1 does not form a completely linear channel with the intake pipe 211, to ensure there is adequate space for the accumulation and redirection of airflow after it exits the intake pipe 211, the distance between the outlet end and the inner wall of the casing 2 is set to be greater than or equal to the diameter of the outlet end. The connection between the intake pipe 211 and the air intake 21 can be understood as either a direct or indirect connection. The intake pipe 211 can be physically connected to the casing 2 through mechanisms such as snap-fittings or could be chemically bonded using adhesives (as shown in FIGS. 21A and 21B, which only depict circular and square channels of the intake pipe 211). Additionally, the intake pipe 211 can be integrally formed with the casing 2. Moreover, the presence of the exhaust pipe 221 facilitates a convenient connection between the outlet 52 of the blower 5 and the respiratory device's casing outlet. The exhaust pipe 221 is configured to connect one end to the outlet 52 of the blower 5 and the other end either to an opening on the device casing or directly through the device casing to the respiratory tubing. The connection between the exhaust pipe 221 and the outlet 52 of the blower 5 can also be understood as being made through either an indirect connection using a third component or a direct connection. To ensure that the gas flowing out from the outlet 52 of the blower 5 can be transmitted through the exhaust pipe 221 steadily and without turbulence, at least a section of the exhaust pipe 221 near the outlet 52 of the blower 5 is configured to be a straight, unbent line, and the ratio of the opening area of the exhaust pipe 221 to the outlet area of the blower 52 is between 85% to 110%. In one implementation, to ensure gas tightness, the exhaust pipe 221 has a sealing component (made from materials such as silicone, rubber, TPE, TPU, or fluororubber) that connects the air outlet 22 to the outlet 52 of the blower 5. To achieve the lowest possible noise level, the axes of the intake pipe 211 and the exhaust pipe 221 are oriented in different directions to block mutual noise interference. Additionally, in one implementation, the air intake 21 has a flexible component 7 including flexible material (as shown in FIG. 22). This flexible component 7 is configured to more effectively capture and eliminate noise carried in the airflow entering through the air intake 21, with flexible materials including silicone, rubber, TPE, TPU, or fluororubber. Due to the flexible geometry and characteristics of the flexible material, it can guide and diffuse the airflow, thereby reducing the speed and pressure of the airflow, which in turn reduces noise production. Thus, at the positions of the air intake 21 and air outlet 22, flexible components made from soft, noise-reducing materials such as silicone and rubber can be used. This approach can effectively reduce noise caused by vibrations from the blower 5, thereby creating a quieter and more comfortable usage environment. In summary, this method not only achieves efficient airflow control but also significantly reduces noise, providing patients with a quieter and more comfortable user experience.

In another implementation, the intake pipe 211 and the casing 2 of the gas passage 1 are integrally formed.

Figure 23:
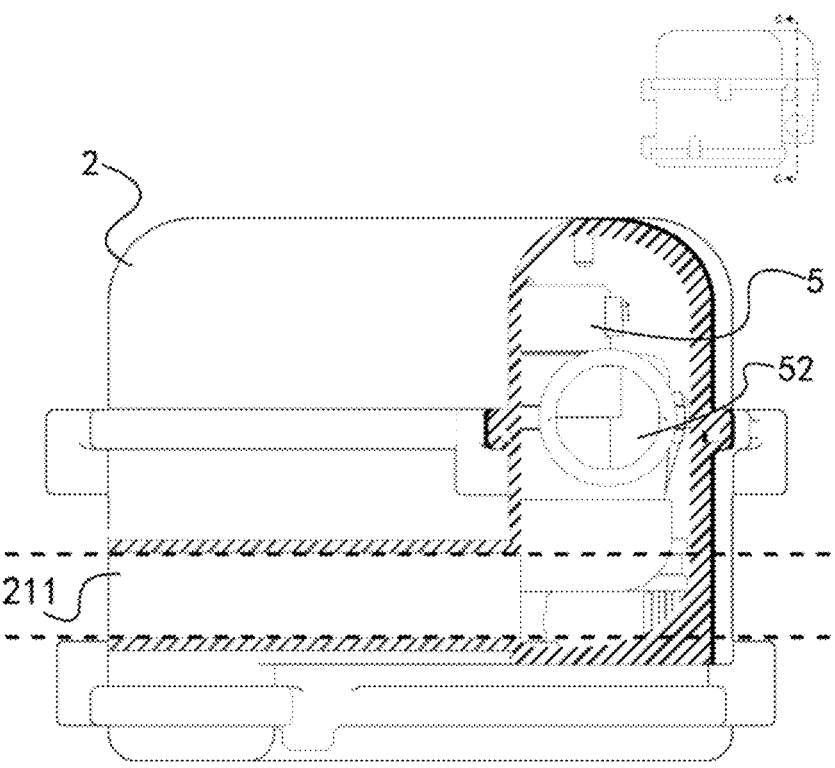
FIG. 23 is a sectional diagram of a gas passage with an intake pipe without tapering, according to an embodiment of the present disclosure.

In another implementation, the intake pipe 211 has no taper (as shown in FIG. 23).

In another implementation, the intake pipe 211 is provided at the edge part of the gas passage 1 (as shown in FIGS. 21A and 21B).

Embodiment 3

Figure 24:
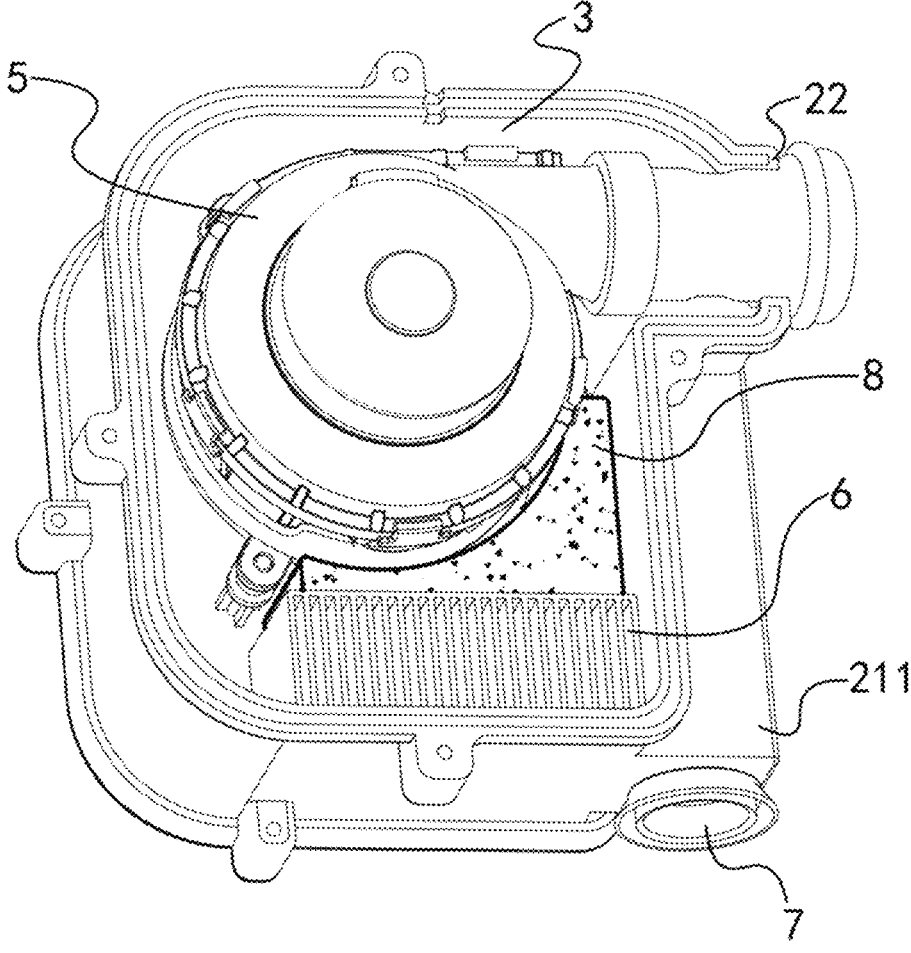
FIG. 24 is a schematic diagram showing the presence of the soundproofing material inside a gas passage according to an embodiment of the present disclosure.
Figure 25:
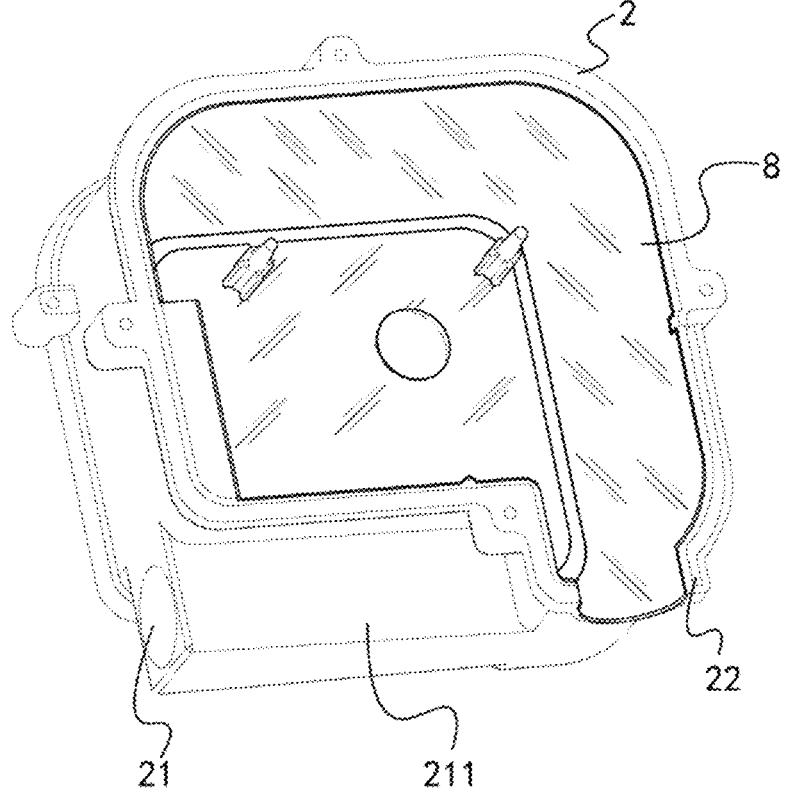
FIG. 25 is a schematic diagram showing the soundproofing material on the inner wall of a gas passage according to an embodiment of the present disclosure.
Figure 26:
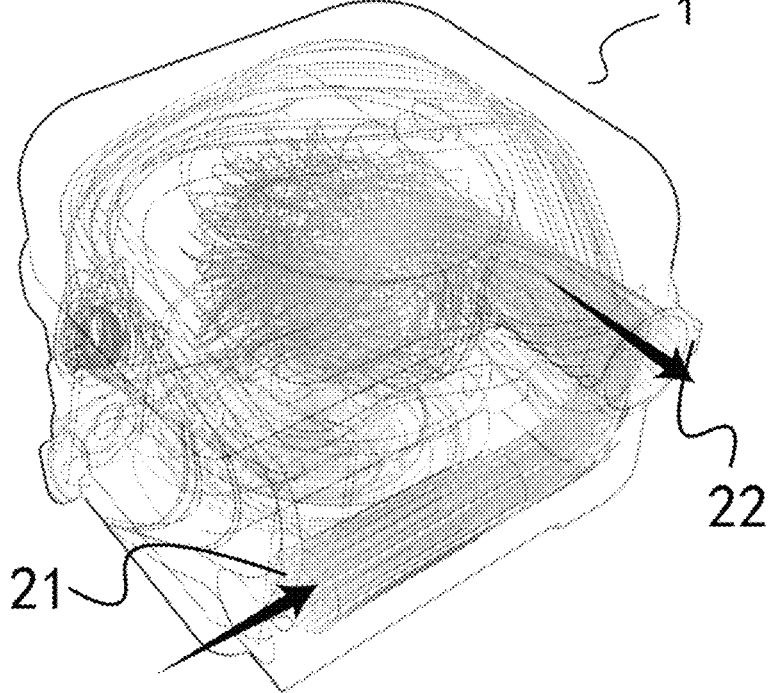
FIG. 26 is a schematic diagram analyzing the airflow path inside a gas passage according to an embodiment of the present disclosure.
Figure 27:
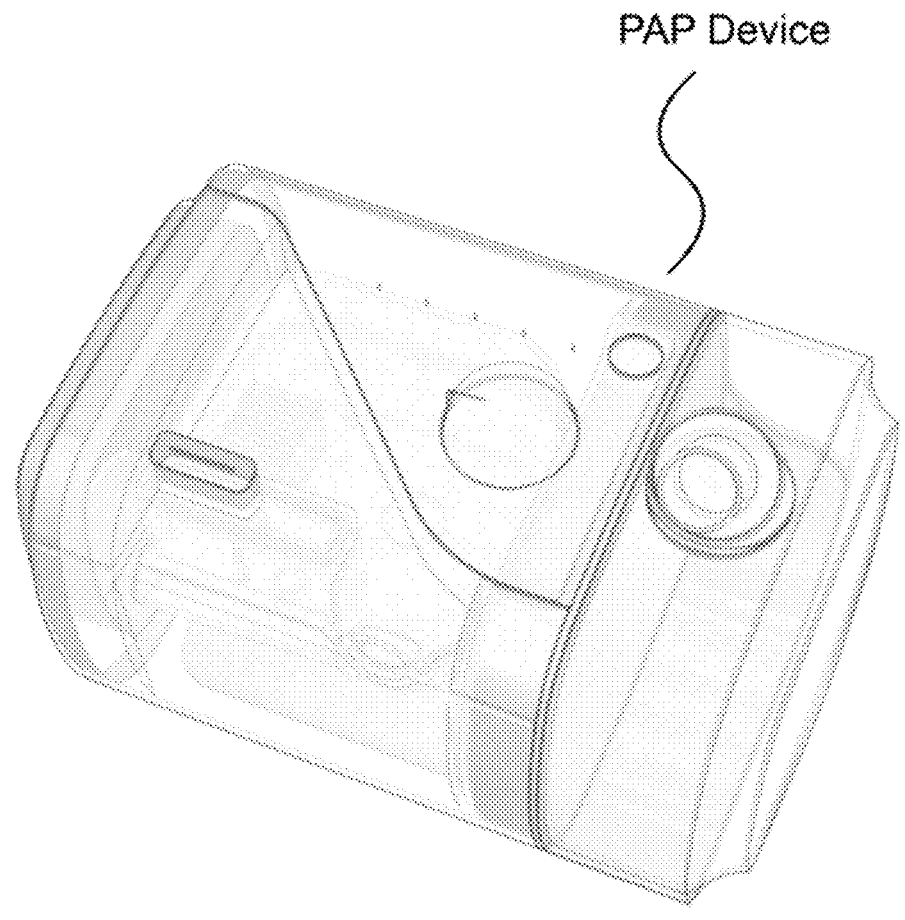
FIG. 27 is a schematic diagram of a PAP device described in this disclosure.

This embodiment provides a gas passage 1 used within a PAP device, as referenced in FIGS. 25-26. This embodiment provides three-dimensional schematic diagrams of the gas passage 1. In the embodiment shown in FIGS. 24-25, differing from Embodiment 1's gas passage 1, the interior of the gas passage 1 discussed herein includes soundproofing materials 8. These special materials absorb and eliminate noise as the airflow passes through, effectively reducing noise. The soundproofing materials 8 may include foam, silicone, or other materials suitable for noise reduction. Currently, foam, silicone, and other efficient soundproofing materials 8 are widely used in noise reduction technologies. Foam, due to its compact structure, effective sound absorption, and moderate cost, is almost universally used for noise reduction in existing gas passages on the market. However, the gas passage 1 of this disclosure has a more efficient noise reduction structure, capable of meeting regulatory noise levels. Thus, when the gas passage 1 of this disclosure houses foam, its structural advantages are more pronounced, achieving a noise reduction and comfort level superior to traditional gas passages 1. However, due to the porous structure of foam, when foam is present inside the gas passage 1, the gas flow through it might cause loss of flow or pressure. To address this issue, this disclosure also explored the possibility of using silicone as an alternative material. Silicone is elastic and soft, so silicone of a certain thickness can also achieve a noise reduction effect similar to foam. Through multiple experiments, it was determined that using silicone materials instead of foam for noise reduction can prevent loss of gas flow or pressure, thereby ensuring the efficient and stable operation of the gas passage 1. In summary, the noise reduction design of the gas passage 1 considers various factors, including noise control, stability, and cost-effectiveness. Regardless of the patient's needs, the various designs of this disclosure offer flexible options to meet different usage scenarios and preferences.

Implementing this disclosure's gas passage offers several beneficial effects:

1. Designing and optimizing multiple structures within the gas passage allows it to achieve superior noise reduction solely through internal structural enhancements. Specifically: (1) Simple and efficient new structures such as ventilation components, intake pipes and flexible components are configured to effectively reduce the noise in each part of the gas passage respectively, thus achieving better noise reduction in the gas passage. a. The specific structure of the ventilation component in this disclosure includes orderly arranged baffles inside and a peripheral wall that shapes its exterior. Compared to existing noise-reducing structure components in gas passages on the market, the ventilation component of this disclosure is simpler, yet its noise reduction effectiveness is not inferior to existing market components. This design not only helps reduce the propagation of noise in the gas passage but also minimizes cross-interference and turbulence of airflow, facilitating a smoother flow of air through the gas passage and reducing energy loss. b. Additionally, this disclosure has been experimentally proven that a conical gas passage has a certain degree of noise reduction effect. Therefore, an intake pipe is installed at the gas passage's air intake and configured as a conical gas passage to achieve better noise reduction. c. Similarly, a flexible component is configured in the same form as the intake pipe and placed at the air intake where the gas supply enters. Since the flexible component is a separate, single structure, it is made of an elastomeric material to further reduce noise. The noise reduction structures of the ventilation component, the intake pipe, and the flexible component are positioned at different locations within the chamber of the gas passage, effectively reducing noise uniformly across various parts of the gas passage, and minimizing the overall noise emitted from the airway. (2) Digital optimization of the internal structure of the gas passage and strategic planning of the placement of its internal components are conducted to achieve better noise reduction more scientifically. Specifically, limiting the distance between the blower and the inner wall of the casing helps isolate the blower from the casing of the gas passage, thereby reducing vibrations and noise, and preventing the creation of small gaps that could produce noise as gas passes through. By regulating the length-to-width ratio and internal gaps of the ventilation components, the optimal noise reduction effect is achieved for this structural configuration in conjunction with the gas passage. Requirements are made for the distance between each opening of each chamber that provides gas flow into the internal chambers of the gas passage and the opposing inner walls of the casing to ensure there is ample space for gas accumulation and directional changes without causing disorder and turbulence. The optimized casing of the gas passage enhances operational efficiency while also reducing gas pressure and flow consumption. Additionally, placing the air intake and air outlet on different planes of the casing effectively reduces noise from the air intake and ensures that this noise is kept away from the patient's ear area, significantly enhancing the overall comfort of the device. Beyond the mentioned advantages, further optimization of the gas passage design and flow characteristics can significantly improve the stability of the device. This means that performance fluctuations and uncertainties during start-up, operation, and shutdown phases will be greatly reduced, further enhancing the operational stability and reliability of the device. These comprehensive benefits not only improve the long-term stability and performance of the device but also effectively reduce safety risks and potential failure rates during operation. (3) By redesigning and optimizing the internal structure of the gas passage from both planar and three-dimensional perspectives, the path of airflow within the gas passage has been increased to achieve superior noise reduction. The length of airflow directly affects the noise levels within the chamber;

shorter airflow paths tend to result in sudden changes in airflow speed and pressure, which can increase the likelihood of noise generation. Conversely, longer airflows gradually slow down the changes in gas speed and pressure over time, thereby reducing noise production. In the planar effect, this disclosure places the blower at the center of the gas passage, causing the airflow entering the chamber housing the blower to flow around it before flowing into other chambers. This arrangement increases the length of the airflow path within the plane, reducing noise. In the three-dimensional effect, in one instance, the internal chambers of the gas passage are designed as upper and lower chambers, allowing the gas to have a vertical path in addition to the planar path. This configuration transforms the airflow path from planar to three-dimensional, noticeably increasing the airflow path. Furthermore, by positioning the ventilation components within the gas passage so that the airflow direction through the ventilation components is vertical, and since the ventilation components are noise-reducing components with a certain height and not on the same plane as the intake and outlet, the airflow from the intake to the outlet undergoes at least three changes in height, meaning the gas flows vertically at least twice. This increases the vertical path and further lengthens the airflow path, providing patients with a quieter and more comfortable user experience.

2. From the patient's perspective, this disclosure not only offers a variety of options but also minimizes the impact on airflow when employing a foamless gas passage design, which not only extends the life of the device but also enhances safety during use. a. In devices utilizing a foamless design, the internal structure of the gas passage has been optimized to significantly reduce airflow resistance. Firstly, through geometric design and streamlined structures with large rounded corners, the space within the gas passage is maximized, ensuring that airflow can move smoothly without obstruction. Secondly, the smooth surface of the inner walls of the gas passage reduces friction between the airflow and the inner walls. This not only increases the speed of air circulation but also helps reduce energy consumption, thereby enhancing the overall performance and efficiency of the device. b. Furthermore, in terms of safety, foamless design is more beneficial for respiratory safety. According to some cases, such as recall events from a certain brand, foam materials used over a long period may release harmful particles under specific conditions, and might even pose a carcinogenic risk. Additionally, if the device is improperly cleaned or stored for long periods in hot and humid conditions, foam materials may degrade and emit harmful gases. Eliminating foam from the design also effectively reduces potential issues with microbial growth and the accumulation of other contaminants within the device. Such design not only raises the hygienic standards of the device but also reduces health risks and maintenance costs for patients during use. A foamless design not only eliminates the risk of blockages that foam in traditional gas passages might cause but also ensures continuity and consistency of the gas passage, further optimizing aerodynamic performance. A foamless gas passage system provides greater flexibility and diversity in the overall design of the device. Beyond traditional foam materials, options like silicone and rubber can be used for other high-performance damping and sound insulation materials to meet specific needs of different patients and application scenarios. This diversified material selection not only enhances the adaptability and compatibility of the device but also broadens its application prospects. c. The foamless design also helps to ensure that the device maintains high levels of performance and quality standards after multiple uses. For example, traditional foam may degrade, deform, or cause blockages over time, or lead to overheating, short-circuiting, or mechanical damage to the device. These issues can pose safety risks and affect the device's performance, but a foamless design eliminates these potential problems, making the device more durable, maintaining efficient operation, and extending its lifespan. Thus, the lifespan of foam is typically more limited compared to other components within the gas passage, so removing foam from the gas passage, on one hand, extends its lifespan. d. This disclosure, with its highly efficient internal noise reduction structures and components, can achieve equivalent noise reduction effects even without foam. However, for some patients, noise reduction might be a more critical factor. Therefore, under the premise of ensuring safety and basic functionality, for patients with stringent noise requirements, the addition of foam can be considered to achieve higher quality noise reduction effects. Devices can be customized based on individual needs; options include adding foam in the device to further reduce noise, as designs with foam can offer superior noise reduction capabilities. In summary, the design of the gas passage considers multiple factors, including noise control, environmental impact, safety, and cost-effectiveness. Whatever the patient's needs, this design provides flexible options to meet various usage scenarios and preferences.

3. From the supplier's perspective, this disclosure reduces costs in multiple aspects and is more economical. Additionally, the foamless interior of the gas passage is environmentally friendly. a. The foamless design strategy inside the gas passage can reduce the costs of material procurement and manufacturing of the device. Since the airflow does not pass through foam, by expanding the range of foam choices and reducing the amount of foam used, production efficiency can be effectively improved, lowering production costs and thereby bringing higher economic benefits. This not only helps enhance the product's market competitiveness but also enables it to gain a larger market share and customer trust in an increasingly competitive market environment. b. The ventilation component of this disclosure is in the form of a single basic body, simpler than existing noise reduction components on the market and made from a single material, making it more economical in terms of material and manufacturing costs. Moreover, due to the simplicity and efficiency of the noise reduction components, the gas passage interior does not require additional complex structures to achieve the desired noise reduction effects with the ventilation component alone. In the absence of foam, the gas passage also eliminates the need for extra structures to secure the foam. Overall, the interior of the gas passage in this disclosure is more streamlined and simpler than existing designs on the market, making it easier to manufacture. From a manufacturer's perspective, both foamless and foam-inclusive modular designs have their advantages. Furthermore, because the foamless design does not need to account for foam degradation or moisture issues over prolonged use, the requirements for storage and transportation are also simpler and more flexible. Environmental concerns are paramount in modern manufacturing, and a foamless gas passage aligns with internationally advocated environmental principles. A foamless gas passage reduces the consumption of limited resources and lessens the environmental impact during the production process.

The embodiments of this disclosure have been described in conjunction with the accompanying drawings, but the disclosure is not limited to the described embodiments. The embodiments presented are illustrative and not restrictive. It must be noted that, as used herein and in the appended claims, the regular forms "a" "an" "the" include their plural equivalents, unless the context clearly dictates otherwise. Those of ordinary skill in the art, inspired by this disclosure and without departing from the spirit and scope of the disclosure as outlined in the claims, can make numerous modifications, all of which are encompassed within the protection of the disclosure.

The invention claimed is:

1. A gas passage for use in a PAP device, the gas passage comprising:
  a passage casing having an air intake extending in a horizontal direction and an air outlet extending in the horizontal direction, configured to encompass and accommodate internal components;
  at least two chambers spaced apart in a vertical direction and configured to provide spaces for gas flow and accumulation, the at least two chambers including a first chamber and a second chamber;
  a blower provided within the first chamber, having an inlet to receive gas and an outlet spaced from the inlet in the vertical direction to allow the gas to flow out; and
  at least one ventilation component configured to communicate with the at least two chambers to allow the gas to flow through the at least one ventilation component;
  wherein the gas forms a primary flow path from the air intake of the passage casing to the air outlet, and wherein the primary flow path has at least three height differences,
  wherein a center of the air intake and a center of the air outlet are at different heights,
  wherein both an ingress to the at least two chambers and an egress from the at least two chambers are provided within the first chamber.

2. The gas passage according to claim 1, wherein the at least one ventilation component within the gas passage takes a form of several ventilation components combined together.

3. The gas passage according to claim 1, wherein the at least one ventilation component includes at least one baffle, and the at least one baffle of the ventilation component is configured to have inclined surfaces.

4. The gas passage according to claim 1, wherein the passage casing includes an inner wall, and a distance between the blower and the inner wall of the passage casing is at least 4 mm.

5. The gas passage according to claim 1, wherein a direction of the gas passing through the at least one ventilation component is parallel or perpendicular to a direction of the gas entering the blower.

6. The gas passage according to claim 1, wherein a length of the primary flow path is at least 160 mm.

7. A gas passage for use in a PAP device, the gas passage comprising:
  a passage casing having an air intake extending in a horizontal direction and an air outlet extending in the horizontal direction, configured to encompass and accommodate internal components;

at least two chambers spaced apart in a vertical direction and configured to provide spaces for gas flow and accumulation, the at least two chambers including a first chamber and a second chamber;

a blower provided within the first chamber, having an inlet to receive gas and an outlet spaced from the inlet in the vertical direction to allow the gas to flow out; and at least one ventilation component, configured to communicate with the at least two chambers to allow the gas to flow through the at least one ventilation component, wherein, the gas flows from the air intake of the passage casing to the air outlet to form a primary flow path with a height difference, wherein an entirety of the air intake is at a different height than the air outlet, wherein both an ingress to the at least two chambers and an egress from the at least two chambers are provided within the first chamber.

8. The gas passage according to claim 7, wherein the passage casing has an inner wall, wherein the at least one ventilation component is provided only within one of the at least two chambers, and wherein the at least one ventilation component includes a first end to allow gas entry and a second end to allow gas exit, and both ends have a distance of at least 5 mm from the inner wall of the passage casing.

9. The gas passage according to claim 7, wherein the at least one ventilation component includes baffles, and a spacing between each of the baffles is between 0.8 mm to 2.2 mm.

10. The gas passage according to claim 7, wherein a height of the at least one ventilation component is at least 10 mm.

11. The gas passage according to claim 7, wherein the gas enters the inlet of the blower either in a straight manner or in a rotation direction of the blower.

12. The gas passage according to claim 7, wherein the at least one ventilation component is configured to be integrally formed with the passage casing.

13. A gas passage for use in a PAP device, the gas passage comprising:

a passage casing having an air intake extending in a horizontal direction and an air outlet extending in the horizontal direction, configured to encompass and accommodate internal components;

at least two chambers spaced apart in a vertical direction and configured to provide spaces for gas flow and accumulation, the at least two chambers including a first chamber and a second chamber;

a blower provided within the first chamber, having an inlet to receive gas and an outlet spaced from the inlet in the vertical direction to allow the gas to flow out; and at least one ventilation component, configured to communicate with the at least two chambers to allow the gas to flow through the at least one ventilation component;

wherein, an axial line of the air intake of the passage casing is not parallel to an axial line of the inlet of the blower;

wherein, the gas flows from the air intake of the passage casing to the air outlet to form a primary flow path with a height difference, wherein an entirety of the air intake is at a different height than the air outlet, and wherein both an ingress to the at least two chambers and an egress from the at least two chambers are provided within the first chamber.

14. The gas passage according to claim 13, wherein the air intake is configured to have a flexible component and the flexible component includes a flexible material.

15. The gas passage according to claim 13, wherein an intake pipe connectable to the air intake is provided at the air intake, and a length of the intake pipe is between 25 mm to 80 mm.

16. The gas passage according to claim 15, wherein the intake pipe is provided at an edge part of the gas passage.

17. The gas passage according to claim 13, wherein a volume of the first chamber is at least three times a volume of the blower.

18. The gas passage according to claim 17, wherein the passage casing includes one of the following materials: polypropylene, polycarbonate, polyethylene terephthalate glycol-modified-1,4-cyclohexanedimethanol ester, polyamide, or polyetheretherketone.

19. A gas passage for use in a PAP device, the gas passage comprising:

a passage casing having an air intake and an air outlet, configured to encompass and accommodate internal components;

at least two chambers configured to provide spaces for gas flow and accumulation, the at least two chambers including a first chamber and a second chamber;

a blower provided within the first chamber, having an inlet to receive gas and an outlet to allow the gas to flow out, wherein the inlet is configured to communicate with one of the at least two chambers that does not house the blower; and at least one ventilation component in a passage between the first chamber and the second chamber and having an inlet end for gas entry and an outlet end for gas exit, wherein both ends are at a distance greater than or equal to 3.45 mm from an inner wall of the passage casing;

wherein, the gas flows from the air intake of the passage casing to the air outlet to form a primary flow path with at least one height difference;

wherein an intake pipe connectable to the air intake is provided at the air intake, and is configured to communicate an external environment with an interior of the passage casing, wherein an outlet pipe connectable to the air outlet is provided at the air outlet, and is configured to receive pressurized airflow from the outlet of the blower, wherein the intake pipe has at least one of the following characteristics:

a. the intake pipe having a draft angle, and the angle being greater than or equal to 0.1°; and b. a length of the intake pipe being between 25 mm to 80 mm, wherein a center of the air intake and a center of the air outlet are at different heights, and wherein both an ingress to the at least two chambers and an egress from the at least two chambers are provided within the first chamber.

20. The gas passage according to claim 19, wherein a distance between the blower and the inner wall of the passage casing is at least 4 mm.

21. The gas passage according to claim 19, wherein a volume of the first chamber is at least three times a volume of the blower.

22. The gas passage according to claim 19, wherein an axial line of the intake pipe is perpendicular to an axial line of the inlet of the blower.

23. The gas passage according to claim 19, wherein a ratio of an opening area of the outlet pipe to an area of the outlet of the blower is between 85% to 110%.

24. The gas passage according to claim 19, wherein an axial line of the intake pipe and an axial line of the outlet pipe have different orientations.

25. The gas passage according to claim 19, wherein the outlet pipe is provided with a sealing component connectable to the outlet pipe, and the sealing component is configured to connect the air outlet to the outlet of the blower.

\* \* \* \* \*